(12) United States Patent
Irimia

(10) Patent No.: US 8,921,122 B2
(45) Date of Patent: Dec. 30, 2014

(54) SYSTEM AND METHOD FOR QUANTITATIVE ASSESSMENT OF BIOLOGICAL MIGRATION BEHAVIOR

(75) Inventor: Daniel Irimia, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 1141 days.

(21) Appl. No.: 12/867,160

(22) PCT Filed: Feb. 11, 2009

(86) PCT No.: PCT/US2009/000890
§ 371 (c)(1),
(2), (4) Date: Jan. 31, 2011

(87) PCT Pub. No.: WO2009/102453
PCT Pub. Date: Aug. 20, 2009

(65) Prior Publication Data
US 2011/0117579 A1    May 19, 2011

Related U.S. Application Data

(60) Provisional application No. 61/065,365, filed on Feb. 11, 2008, provisional application No. 61/111,213, filed on Nov. 4, 2008.

(51) Int. Cl.
| | | |
|---|---|---|
| *G01N 33/558* | (2006.01) | |
| *G01N 33/50* | (2006.01) | |
| *B01L 3/00* | (2006.01) | |
| *G01N 33/543* | (2006.01) | |
| *G01N 33/49* | (2006.01) | |

(52) U.S. Cl.
CPC ......... *G01N 33/491* (2013.01); *G01N 33/5029* (2013.01); *B01L 2200/10* (2013.01); *B01L 2400/0421* (2013.01); *B01L 3/502776* (2013.01); *G01N 33/54366* (2013.01); *B01L 2400/0442* (2013.01); *B01L 2300/0887* (2013.01); *B01L 2300/0816* (2013.01); *B01L 2400/043* (2013.01); *B01L 2300/0636* (2013.01); *Y10S 436/805* (2013.01); *Y10S 436/807* (2013.01)

USPC ........ 436/514; 422/400; 422/502; 435/288.4; 435/288.5; 435/288.7; 436/805; 436/807

(58) Field of Classification Search
None
See application file for complete search history.

(56) References Cited

U.S. PATENT DOCUMENTS 5,086,476 A * 2/1992 Bacus .......................... 382/133
5,744,366 A    4/1998 Kricka et al.
(Continued)

FOREIGN PATENT DOCUMENTS

| WO | 02/44730 | 6/2002 |
| WO | 2009/102453 | 8/2009 |
| WO | WO 2010/108095 | 9/2010 |

OTHER PUBLICATIONS

Albini and Benelli "The chemoinvasion assay: a method to assess tumor and endothelial cell invasion and its modulation" Nat Protoc. 2(3):504-511 (2007).

(Continued)

*Primary Examiner* — Chris L Chin
(74) *Attorney, Agent, or Firm* — Fish & Richardson P.C.

(57) ABSTRACT

The present invention provides systems and methods for assessing migration behavior of biological particles, such as neutrophils, under the effect of a gradient. The systems can include one or more migration chambers, one or more gradient sources configured to generate particular gradients, e.g., of chemokines or the like across the width of the migration chamber, and a detection arrangement that is configured to determine spatial profiles across the migration chamber that indicate the extent of migration.

32 Claims, 13 Drawing Sheets

(56) References Cited

U.S. PATENT DOCUMENTS

| | | |
|---|---|---|
| 6,921,660 B2 | 7/2005 | Kirk et al. |
| 7,326,563 B2 | 2/2008 | Kim et al. |
| 7,374,906 B2 | 5/2008 | Kirk et al. |
| 2005/0271548 A1 | 12/2005 | Yang et al. |
| 2011/0117579 A1 | 5/2011 | Irimia |
| 2012/0094325 A1 | 4/2012 | Irimia |

OTHER PUBLICATIONS

Beningo et al. "Responses of fibroblasts to anchorage of dorsal extracellular matrix receptors" Proc Natl Acad Sci USA 101(52):18024-18029 (2004).
Bovin and Gabius "Polymer-immobilized carbohydrate ligands: Versatile Chemical Tools for Biochemistry and Medical Sciences" Chemical Society Reviews 24(6):413-421 (1995).
Boyden "The Chemotactic Effect of Mixtures of Antibody and Antigen on Polymorphonuclear Leucocytes" Journal of Experimental Medicine 115 (3):453-466 (1962).
Brandley and Schnaar "Cell-Surface Carbohydrates in Cell Recognition and Response" Journal of Leukocyte Biology 40:97-111 (1986).
Carmignani et al. "Intraperitoneal cancer dissemination: Mechanisms of the patterns of spread" Cancer Metastasis Rev. 22:465-472 (2003).
Cavallaro and Christofori "Cell adhesion and signalling by cadherins and Ig-CAMs in cancer" Nature Reviews Cancer 4:118-132 (2004).
Chiang and Massague "Molecular Basis of Metastasis" N. Engl J Med. 359 (26):2814-2823 (2008).
Condeelis and Segall "Intravital imaging of cell movement in tumours" Nature Reviews Cancer 3:921-930 (2003).
Decaestecker et al. "Can anti-migratory drugs be screened in vitro? A review of 2D and 3D assays for the quantitative analysis of cell migration" Medicinal Research Reviews 27(2):149-176 (2007).
Demou and McIntire "Fully automated three-dimensional tracking of cancer cells in collagen gels: Determination of motility phenotypes at the cellular level" Cancer Research 62(18):5301-5307 (2002).
Even-Ram and Yamada "Cell migration in 3D matrix" Current Opinion in Cell Biology 17:524-532 (2005).
Feki et al. "Dissemination of intraperitoneal ovarian cancer: Discussion of mechanisms and demonstration of lymphatic spreading in ovarian cancer model" Crit Rev Oncol Hematol. 72:1-9 (2009).
Friedl and Wolf "Tumour-cell invasion and migration: Diversity and escape mechanisms" Nature Reviews Cancer 3:362-374 (2003).
Gerhardt and Semb "Pericytes: gatekeepers in tumour cell metastasis?" J Mol Med 86:135-144 (2008).
Giese and Westphal "Glioma invasion in the central nervous system" Neurosurgery 39(2):235-252 (1996).
Hanahan and Weinberg "The Hallmarks of Cancer" Cell 100:57-70 (2000).
Irimia et al. "Adaptive-Control Model for Neutrophil Orientation in the Direction of Chemical Gradients" Biophysical Journal 96:3897-3916 (2009).
Irimia et al. "Polar stimulation and constrained cell migration in microfluidic channels" Lab Chip 7:1783-1790 (2007).
Irimia et al. "Microfluidic system for measuring neutrophil migratory responses to fast switches of chemical gradients" Lab Chip 6:191-198 (2006).
Irimia et al. "Universal Microfluidic Gradient Generator" Analytical Chemistry 78(10):3472-3477 (2006).
Keenan and Folch, "Biomolecular gradients in cell culture systems" Lab Chip 8:34-57 (2008).
Keenan et al. "Microfluidic 'jets' for generating steady-state gradients of soluble molecules on open surfaces" Applied Physics Letters 89:114103 (2006) (3 pages).
Kuntz and Saltzman, "Neutrophil Motility in Extracellular Matrix Gels: Mesh Size and Adhesion Affect Speed of Migration" Biophysical Journal 72:1472-1480 (1997).
Lammermann et al. "Rapid leukocyte migration by integrin-independent flowing and squeezing" Nature 453:51-55 (2008).
Lee et al. "Three-dimensional micropatterning of bioactive hydrogels via two-photon laser scanning photolithography for guided 3D cell migration" Biomaterials 29:2962-2968 (2008).
Levy et al. "Endoscopic ultrasound fine-needle aspiration detection of extravascular migratory metastasis from a remotely located pancreatic cancer" Clin Gastroenterol Hepatol. 7:246-248 (2009).
Lugassy and Barnhill "Angiotropic melanoma and extravascular migratory metastasis: A review" Adv Anal Pathol. 14:195-201 (2007).
Malawista et al. "Random locomotion and chemotaxis of human blood polymorphonuclear leukocytes from a patient with leukocyte adhesion deficiency-1: Normal displacement in close quarters via chimneying" Cell Motil. Cytoskeleton 46:183-189 (2000).
Overall and Lopez-Otin "Strategies for MMP inhibition in cancer. Innovations for the post-trial era" Nat Rev Cancer 2:657-672 (2002).
Raeber et al. "Molecularly engineered PEG hydrogels: a novel model system for proteolytically mediated cell migration" Biophysical Journal 89:1374-1388 (2005).
Rhee et al. "Microtubule function in fibroblast spreading is modulated according to the tension state of cell-matrix interactions" Proc Natl Acad Sci USA 104(13):5425-5430 (2007).
Sahai "Illuminating the metastatic process" Nature Reviews Cancer 7:737-749 (2007).
Sahai and Marshall "Differing modes of tumour cell invasion have distinct requirements for Rho/ROCK signalling and extracellular proteolysis" Nat Cell Biol. 5(8):711-719 (2003).
Sahai et al. "Simultaneous imaging of GFP, CFP and collagen in tumors in vivo using multiphoton microscopy" BMC Biotechnology 5(14):1-9 (2005).
Savage et al. "Why does cytotoxic chemotherapy cure only some cancers?" Nat Clin Pract Oncol. 6:43-52 (2009).
Sporn "The war on cancer" Lancet. 347:1377-1381 (1996).
Sugarbaker et al. "Gastrectomy, peritonectomy, and perioperative intraperitoneal chemotherapy: The evolution of treatment strategies for advanced gastric cancer" Semin Surg Oncol. 21:233-248 (2003).
Tan et al. "Mechanisms of transcoelomic metastasis in ovarian cancer" Lancet Oncol. 7:925-934 (2006).
Tanos and Rodriguez-Boulan "The epithelial polarity program: machineries involved and their hijacking by cancer" Oncogene 27:6939-6957 (2008).
Todaro et al. "Initiation of Cell Division in a Contact-Inhibited Mammalian Cell Line" J. Cell and Comp. Physiol. 66:325-333 (1965).
Vermeer et al. "Segregation of receptor and ligand regulates activation of epidermal growth factor receptor" Nature 422:322-326 (2003).
Wang et al. "Reciprocal interactions between beta1-integrin and epidermal growth factor receptor in three-dimensional basement membrane breast cultures: a different perspective in epithelial biology" Proc Natl Acad Sci USA. 95:14821-14826 (1998).
Yamada and Cukierman "Modeling tissue morphogenesis and cancer in 3D" Cell 130:601-610 (2007).
Yarrow et al. "A high-throughput cell migration assay using scratch wound healing, a comparison of image-based readout methods" BMC Biotechnology 4(21):1-9 (2004).
Zahm et al. "Cell migration and proliferation during the in vitro wound repair of the respiratory epithelium" Cell Motil. Cytoskeleton 37:33-43 (1997).
International Search Report and Written Opinion dated Oct. 26, 2010 issued in International application No. PCT/US2010/027980.
International Preliminary Report on Patentability dated Sep. 29, 2011 issued in International application No. PCT/US2010/027980.
International Search Report and Written Opinion dated Sep. 28, 2009 from International application No. PCT/US2009/000890.

* cited by examiner

SYSTEM AND METHOD FOR QUANTITATIVE ASSESSMENT OF BIOLOGICAL MIGRATION BEHAVIOR

This application is the national stage of International Application Number PCT/US2009/000890, filed on Feb. 11, 2009, which is based on and claims the benefit of the filing dates of U.S. Provisional Application No. 61/065,365, filed Feb. 11, 2008, and U.S. Provisional Application No. 61/111,213, filed Nov. 4, 2008, the contents of which as filed are incorporated herein by reference in their entirety.

GOVERNMENT SUPPORT

This invention was made with Government support under Grant No. (s) EB002503 awarded by the National Institutes of Health. The Government has certain rights in this invention.

FIELD OF THE INVENTION

The present invention relates to systems and methods for assessing migration responses, including chemotactic effects, in biological systems. The systems and methods can provide quantitative determination of migration responses in a variety of gradients and can be used with very small fluid samples on the order of microliters.

BACKGROUND OF THE INVENTION

There is an increasing interest in so-called "lab-on-a-chip" technologies for cell-based, scientific, and/or clinical applications. Such techniques can integrate various procedures on small devices, including, e.g., primary sample collection, sample processing, and/or data analysis. Lab-on-a-chip devices often use microfluidic structures to process small samples and can facilitate more rapid processing of samples. Such devices and methods can often be used without a need for extensive lab support and thus may be well suited for field and point-of-care applications.

Migration of biological species in response to certain environmental factors can be very important in understanding various mechanisms that occur in the body and in developing effective treatments for various conditions. Neutrophil directional migration in response to soluble chemoattractant gradients is a critical process during the response of the innate immune against bacterial infection. Also known as chemotaxis, it plays a significant role in several other physiological processes such as inflammation, wound healing, metastasis, atherosclerosis, arthritis etc. With recent developments in microfluidic technologies, cell migration research has gained significant attention in recent years and a variety of in vitro migration assays have been developed. One major challenge for these assays is the isolation of neutrophils from whole blood without activating them or altering their phenotype. The most commonly used isolation procedures involve Ficoll-Hypaque centrifugation, erythrocyte lysis or the combination of these two techniques. Alternatively, neutrophils can be separated from whole blood by negative immunomagnetic separation techniques which deplete all unwanted cells by selective capture on functionalized magnetic beads. These techniques require large volumes of whole blood (of the order of milliliters) and are prone to mechanical, osmotic or thermal shocks to which neutrophils are highly sensitive. While recent studies involving high speed microfluidic lysis process can yield 98-100% leukocytes with minimal activation, the method still requires a centrifugation step for debris removal, which is difficult to implement on the chip. The effects of cell lysate contaminat on neutrophils' responsiveness to subsequent chemotactic gradients are also unknown.

A second critical challenge in studying neutrophil chemotaxis is establishing more complex gradient generation schemes to study sequential effects of different chemokines or activity of anti-inflammatory agents. Since the development of the Boyden chamber in 1962, several other techniques including micropipette generated gradients, hydrogel based assay, Zigmond chamber and Dunn chamber have been proposed for studying chemotactic responsiveness of many cells, including neutrophils, to artificial chemical gradients. However, many of these assays pose limitations of gradient nonlinearity and spatial/temporal instability making repeatability of the experimental conditions difficult to control. While some of these methods are unsuitable for observing single cell responses (e.g., Boyden chamber), others lack the capability to support multifactor combinatorial gradients or only offer short lived gradients (e.g., Dunn chamber). More recently, microfluidic gradient generators have greatly evolved and a number of models categorized as parallel-flow or flow-resistive gradient generators have been proposed to perform in vitro chemotaxis. Although many of the microfluidic techniques succeed in eliminating the issues related to quantification as well as spatial and temporal stability of gradients, they fail either to provide dynamic control over the established gradients or to independently generate combinatorial gradients of multiple chemokines. Moreover, none of these techniques were able to provide a complete assay for combined capture and migration analysis without undergoing additional isolation steps.

The directed migration of neutrophils in vivo involves sequential signaling events to guide them from blood stream into the tissue near the site of injury. The endothelium, when exposed to inflammation signals, may express cell adhesion molecules, such as P-selectin and E-selectin, and can present chemoattractants, such as IL-8, for which complementary receptors exist on leukocyte surface. This mechanism can lead to localization of circulating neutrophils towards the inner wall of blood vessels where hemodynamic shear stresses may be smaller, and the cells can begin to roll and migrate based on, e.g., weak transient binding of CAMs with cell receptors. The presence of inflammation signals on the endothelial cells may later induce the expression of integrin receptors, which can lead to cellular arrest followed by transmigration of neutrophils into the tissue.

The commonly used neutrophils isolation methods such as Ficoll-Hypaque isolation and immunomagnetic separation work reliably, however, they require over an hour to isolate neutrophils and demand several milliliters of whole blood. These methods are not suited for studies where rat or mice models are used due to the lower volumes of blood samples available in these smaller animals (only a few milliliters). Such experiments often mandate sacrificing the animal in order to extract enough blood, and make prolonged monitoring of the animals very difficult to accomplish. Recently, microfluidic devices coated with antibodies have been demonstrated for the isolation of leukocytes from whole blood. These devices require only small volumes of blood and accomplish the isolation of targeted leukocyte subpopulation in less than 10 minutes. One limitation of these devices, in the context of the chemotaxis assays, is that the binding of the cells to the antibody coated surface is strong and practically irreversible, prohibiting their use for chemotaxis assays.

The ability to visualize moving cells in a chemotaxis assay can be important for differentiating between chemotaxis and chemokinesis (e.g., directional vs. random motility). Further, visualization of cell morphology changes upon exposure of cells to chemokines and lipid mediators may also be important in understanding the mechanisms by which such substances can affect cell migration. Conventional clinical chemotaxis assays (e.g., Boyden chambers) may not provide direct visualization of cells.

Microfluidic gradient generators have been developed or proposed using gradient techniques such as, e.g., parallel-flow and flow-resistive gradient generators to perform in vitro chemotaxis. Such microfluidics devices and techniques are described, e.g., in T. M. Keenan and A. Folch, Lab on a Chip, 2008, 8, 34-57; D. Irimia et al., Lab on a Chip, 2006, 6, 191-198; T. M. Keenan et al., Applied Physics Letters, 2006, 89; and R. M. Kuntz and W. M. Saltzman, Biophysical Journal, 1997, 72, 1472-1480. Although some of these techniques may improve performance issues relating to spatial and temporal stabilities of gradients, they generally do not provide dynamic control over established gradients and/or allow independent, combinatorial gradients of multiple chemokines or other materials to be generated. Moreover, none of these techniques or devices provides a complete assay for migration analysis, optionally combined with capture techniques, without performing additional isolation steps.

Accordingly, there is a need for improved methods and devices for quantitative analysis of migration behavior in biological samples.

SUMMARY OF THE INVENTION

According to the present invention, exemplary systems and processes are provided for assessing migration behavior of biological particles, e.g., chemotaxis, in gradients. Such analyses can be performed rapidly, e.g., in less than about 10-20 minutes, and can use very small samples, e.g., tens of microliters or less. The exemplary systems can be provided in compact form; e.g., it may be provided on a conventional glass slide or the like.

Embodiments of the systems presented herein can provide analyses of migration behavior using very small samples, e.g., about 5-10 µL of whole blood, that can be easily obtained from a finger prick or a small incision in the tail vein of a rat. Moreover, a procedure that includes blood drawing and capturing of certain cells for subsequent analysis of their migration behavior can be performed in short times, e.g., on the order of about 5-10 minutes. Such features can provide a significant advantage in chemotaxis studies where fast isolation and loading of primary neutrophils can be performed in a single step prior to the migration analysis. For complex situations involving more than two chemokines or other migration-modifying substances, further exemplary embodiments of the present invention can include multiple gradient networks to suit the requirements for combinatorial chemotaxis.

In one aspect, a system is provided that allows quantitative determination of migration by providing a sample of biological particles in a migration chamber. Predetermined gradients of one or more substances that can affect migration can be provided in a lateral direction across the migration chamber. Such gradients can be provided by introducing one or more substances that affect migration behavior into gradient chambers, e.g., provided along the lateral sides of the migration chamber. The gradients can be constant or variable, e.g., in the chemicals employed and/or the spatial or temporal profile of the gradient. For example, gradients of two or more substances can be provided successively in the migration chamber, with a rapid temporal transition between gradients. Such gradients can be independent of each other, may increase in the same or in different directions, e.g., the opposite direction, and may further have different chemical compositions.

Gradients other than chemical gradients may also be employed. For example, exemplary systems in accordance with embodiments of the present invention may produce a thermal, light, magnetic, and/or electrical gradient in the migration chamber.

The exemplary system can further include one or more valves to control the introduction and movement of the sample and other solutions, e.g., those employed to create the gradient, buffer solutions, and the like.

Further exemplary embodiments of the system include a functionalized surface that includes a binding moiety. This functionalized surface can facilitate capture and isolation of desired biological particles from a sample and subsequent migration analysis of the isolated particles. For example, exemplary systems in accordance with the present invention can be used to isolate neutrophils from blood samples using surfaces treated with a neutrophil binding moiety, e.g., an antibody, P-selectin, E-selectin, V-CAM, or fibronectin.

Analysis of effects of chemokine gradients on migration of captured neutrophils can be performed using exemplary systems and methods in accordance with the invention. Compounds that affect migration of neutrophils and may be used in embodiments of the present invention include, e.g., chemokines (e.g., ELR-positive CXC chemokines such as interleukin-8 (IL-8)), leukotriene B4, zymosan-activated serum, and N-formylated peptides (e.g., N-formyl-methionyl-leucyl-phenylalanine (fMLP)). The present invention may also be employed to measure the effects of compounds (e.g., drugs) that interfere with or otherwise affect neutrophil migration.

In addition, exemplary systems and devices of according to the present invention can include a detector that automatically measures spatial information associated with the biological particles within the migration chamber. Such spatial information can include, e.g., a spatial distribution or profile of particles, particle locations or coordinates within the migration chamber, etc. The spatial information may be obtained at a single time or at several different times and may further be associated with one or more exposure intervals of the particles to the gradients. An exemplary detector includes a plurality of components, e.g., optical and/or electrical, e.g., impedance or conductance, detectors. The system can further include a plurality of channels distributed across the migration chamber (or a portion thereof) to facilitate detection of individual particles as they pass through the channels.

In one aspect, the invention features a system for assessing migration of biological particles in a gradient and including at least one migration chamber configured to contain a biological sample having a plurality of the biological particles; at least one gradient arrangement configured to provide at least one predetermined gradient within the migration chamber; and a detection arrangement configured to determine spatial information associated with the biological particles within the migration chamber. The spatial information of the biological particles relates to the migration of the biological particles based on the at least one predetermined gradient.

In a related aspect, the invention features a system for assessing migration of biological particles in a gradient and including at least one migration chamber configured to contain a biological sample having a plurality of the biological particles, wherein a surface of the migration chamber comprises a binding moiety for the biological particles; at least one gradient arrangement configured to provide at least one predetermined gradient within the migration chamber; and a detection arrangement configured to determine spatial information associated with the biological particles within the migration chamber. The spatial information of the biological particles relates to the migration of the biological particles based on the at least one predetermined gradient.

In another aspect, the invention features a system for assessing migration of biological particles in a gradient and including at least one migration chamber configured to contain a biological sample having a plurality of the biological particles; at least one gradient arrangement configured to provide at least one predetermined gradient within the migration chamber; and a detection arrangement comprising a plurality of detectors arranged at an end of the migration chamber and configured to determine spatial information associated with the biological particles within the migration chamber. The spatial information of the biological particles relates to the migration of the biological particles based on the at least one predetermined gradient.

In certain embodiments of the invention, the volume of the biological sample is less than about 20 μL, less than about 10 μL, or less than about 5 μL. In other embodiments, a dimension of the at least one migration chamber is less than about 1 mm.

In other embodiments, the detection arrangement includes at least one of an optical microscope or a digital imaging arrangement. In these embodiments, at least a portion of the at least one migration chamber is configured to facilitate optical observation of the biological particles using the detection arrangement. In an alternative embodiment, the detection arrangement includes a plurality of sensors provided proximal to at least a portion of the at least one migration chamber, e.g., in a distal portion. The plurality of sensors may be located across a lateral width of the at least one migration chamber. At least one of these sensors may include an optical sensor (e.g., including an LED or a photodetector) configured to detect at least one biological particle. In other embodiments, at least one sensor includes an electrical sensor, e.g., configured to detect at least one biological particle based on at least one of an impedance signal or a conductance signal. The detection arrangement may further include a plurality of channels provided within a portion of the at least one migration chamber, e.g., with at least one sensor associated with each channel. Such channels may be configured to allow at least one biological particle to pass through. Each sensor associated with a particular channel may also be configured to detect each biological particle passing through the particular channel.

Examples of spatial information determined by the system include at least one of a spatial distribution, a profile, a location, and/or a coordinate associated with the plurality of the biological particles within the at least one migration chamber. The information may be based on the spatial locations obtained at a particular time or at a plurality of times.

The detection arrangement may be configured to provide signals based on spatial locations of at least a portion of the biological particles within the at least one migration chamber to a processing arrangement.

In certain embodiments, the at least one predetermined gradient is at least one of a temperature gradient, light intensity gradient, an electrical field gradient, and/or a magnetic field gradient. In other embodiments, the at least one predetermined gradient includes at least one gradient in concentration of at least one substance across at least a portion of the at least one migration chamber, e.g., across a lateral width of the at least one migration chamber. The at least one gradient arrangement may include a gradient chamber configured to contain a particular solution including the at least one substance, and the system may further include a valve configured to control a flow of the solution between the gradient chamber and the migration chamber. The at least one gradient arrangement may further include a second gradient chamber configured to contain a further solution, and the system may further include a second valve configured to control a flow of the further solution between the second gradient chamber and the migration chamber. In embodiments with a further solution, it may include at least one of the at least one substance or a further substance. The further solution may also include the at least one substance, and an average concentration of the at least one substance in the particular solution is different than the average concentration of the at least one substance in the further solution. In certain embodiments, at least one of the valve and/or the second valve can be operated to change the gradient within at least a portion of the at least one migration chamber in a predetermined manner at a particular time. The at least one substance and/or the further substance includes, for example, at least one of a chemokine and/or a chemoattractant or at least one of a CC chemokine, CXC chemokine, C chemokine, CX3C chemokine, ELR-positive CXC chemokine, interleukin-8, leukotriene B4, zymosan-activated serum, an N-formylated peptide, MCP-1, CCL28, CCL5, CXCL13, XCL1, XCL2, fractalkine C5a, SDF1, and/or N-formyl-methionyl-leucyl-phenylalanine. The further substance may also include a chemical species capable of inhibiting migration of the biological particles.

In certain embodiments, a surface of the migration chamber is configured to at least one of preferentially bind and/or isolate the biological particles from the biological sample. The surface may include at least one binding moiety capable of binding to the biological particles. In one embodiment, the biological particles are neutrophils, and the at least one binding substance comprises at least one of an antibody, a selectin, P-selectin, E-selectin, V-CAM, and/or fibronectin. Other at least one binding substance include a carbohydrate-binding proteins capable of binding to at least one of a glycoprotein and/or a glycolipids present on a surface of the biological particles. The surface of the migration chamber may be further configured to release the biological particles bound thereto when a releasing solution is introduced into the migration chamber. A bond between the binding moiety and the surface may also be chemically, electrochemically, or photolabile.

The biological sample includes, for example, whole blood, e.g., that does not include an anticoagulant substance. Other biological sample include at least one of lymph, ascites, semen, saliva, urine, and/or cerebrospinal fluid.

Exemplary biological particles include at least one of monocytes, lymphocytes, platelets, trombocytes, circulating tumor cells, circulating stem cells, endothelial precursor cells, sperm cells, yeast, slime mold, Dictyostelium, hepatocytes, neurons, cancer cells, fibroblasts, endothelial cells, and/or dendritic cells.

The system may include at least one of glass, silicon, and/or poly(dimethylsiloxane) or steel, nickel, poly(methylmethacrylate) (PMMA), polycarbonate, polystyrene, polyethylene, a polyolefin, and/or a silicone.

The system may also include a sample valve configured to controllably introduce at least a portion of the biological sample into the migration chamber.

The invention further features a method for assessing migration of biological particles in a gradient by providing a biological sample in a system as described herein; providing at least one predetermined gradient within the migration chamber; and determining spatial information associated with the biological particles within the migration chamber. The spatial information of the biological particles relates to the migration of the biological particles based on the at least one predetermined gradient. In preferred embodiments, the biological sample is less than about 20 µL, e.g., less than about 10 µL.

In certain embodiments, the biological particles are neutrophils; the sample is from a subject suffering from or suspected of suffering from ischemia-reperfusion injury; ischemic stroke; myocardial infarction; kidney ischemia reperfusion after transplant/trauma/blood loss; sterile inflammation due to neutrophil infiltration; severe asthma; colitis; inflammatory bowel disease; periodontitis; retinopathy; bone marrow transplant; monitoring graft versus host disease; neonatal infection; infection of a patient over 60 years of age; cancer treated with chemotherapy; long term, nonspecific immunosuppressive treatment; arthritis, post-transplantation; sepsis; burn injury; and clozepine treatment; and the spatial information provides diagnostic information for the patient.

The method may further include using at least one of selectively binding and/or isolating the biological particles within the migration chamber, e.g., wherein a surface of the migration chamber is functionalized with a binding moiety for the biological particles.

In one embodiment, the biological sample includes whole blood, the biological particles are neutrophils, and the binding moiety includes at least one of an antibody, selectin, P-selectin, E-selectin, V-CAM, and/or fibronectin. The at least one gradient is, for example, provided across a lateral width of the at least one migration chamber. The method may further include at least two gradients across a lateral width of the at least one migration chamber, e.g., where each of the at least two gradients is provided at a different time. The gradient includes, for example, a concentration gradient of at least one substance, e.g., at least one of a chemokine and/or a chemoattractant. Exemplary substances include at least one of a CC chemokine, CXC chemokine, C chemokine, CX3C chemokine, ELR-positive CXC chemokine, interleukin-8, leukotriene B4, zymosan-activated serum, an N-formylated peptide, MCP-1, CCL28, CCL5, CXCL13, XCL1, XCL2, fractalkine C5a, SDF1, and/or N-formyl-methionyl-leucyl-phenylalanine. The at least one the at least one gradient may include a concentration gradient of a chemical species capable of inhibiting migration of the biological particles.

Preferably, the method is completed within about 20 minutes of sample acquisition.

In other embodiments, the at least one gradient includes a candidate therapeutic agent, and the spatial information is indicative of the effect of the candidate therapeutic agent on the migration of the biological particles.

Exemplary biological particles assayed in the methods include monocytes, lymphocytes, platelets, trombocytes, circulating tumor cells, circulating stem cells, endothelial precursor cells, sperm cells, yeast, slime mold, Dictyostelium, hepatocytes, neurons, cancer cells, fibroblasts, endothelial cells, and/or dendritic cells.

In further embodiments, exemplary systems and methods of the present invention may allow direct visual observation of migration behavior of biological particles in the migration chamber using optical techniques such as, e.g., digital cameras and/or image acquisition systems.

In another aspect, embodiments of the present invention provide methods for rapid quantitative analysis of migration effects that require small biological samples on the order of tens of microliters or less using the various exemplary systems described above.

In addition to gradients, systems of the invention may also employ other solutions or reagents, e.g., including detection agents to visualize biological particles (either on the surface or internally), reagents to lyse or fix particles, and/or reagents to release particles bound to a surface.

A "biological particle" as used herein generally refers to, but is not limited to, any species of biological origin that is insoluble in aqueous media on the time scale of sample acquisition, preparation, storage, and analysis. Examples of biological particles include cells (e.g., animal cells, plant cells, bacteria, protists, and fungal cells, e.g., yeast) and viruses.

The term "chamber" as used herein generally refers to, but is not limited to, any designated portion of a microfluidic channel, e.g., where the cross-sectional area is greater, less than, or the same as channels entering and exiting the chamber. A chamber may be separable from another portion of a microfluidic device, so that passage of material (e.g., a fluid) between the chamber and other portion can be constrained or controlled. Such separation may be effected by valves. Separation between chambers may optionally be partial (e.g., where cells or other particles cannot pass between adjacent chambers, but fluids may pass between them). In preferred embodiments, a "migration chamber" is sized to house biological particles of interest and allow the particles to migrate, e.g., for at least two lengths of the particles.

The term "channel" as used herein generally refers to, but is not limited to, a gap through which fluid may flow. A channel may be, for example, a capillary, a conduit, a trench or recessed groove in a surface or substrate, or a strip or other area of a hydrophilic material or coating on a hydrophobic surface such that aqueous fluids may be confined to the hydrophilic area.

The term "microfluidic" device as used herein generally refers to, but is not limited to, a device having a channel or chamber with at least one dimension of less than about 1 mm.

The term "arrangement" as used herein generally refers to, but is not limited to, components and their configurations necessary to achieve the stated purpose. For example, a detection arrangement includes at least a detector; a gradient arrangement includes at gradient source; and a processing arrangement includes at least a computer processor.

The term "releasing solution" as used herein generally refers to, but is not limited to, a solution whose introduction into a migration chamber result in release of biological particles from a surface. The release may be effected by an increase in pressure, shear force, or chemical composition (e.g., pH or an enzyme).

These and other objects, features, and advantages of the present invention will become apparent upon reading the following detailed description of embodiments of the invention, the drawings, and the claims.

DETAILED DESCRIPTION

Systems and Devices

Embodiments of the present invention provide devices for performing analysis of migration behavior of biological particles. Such biological particles can include, e.g., neutrophils, monocytes, lymphocytes, platelets, trombocytes, circulating tumor cells, circulating stem cells, endothelial precursor cells, sperm cells, yeast, slime mold, Dictyostelium, hepatocytes, and/or neurons.

Figure 1:
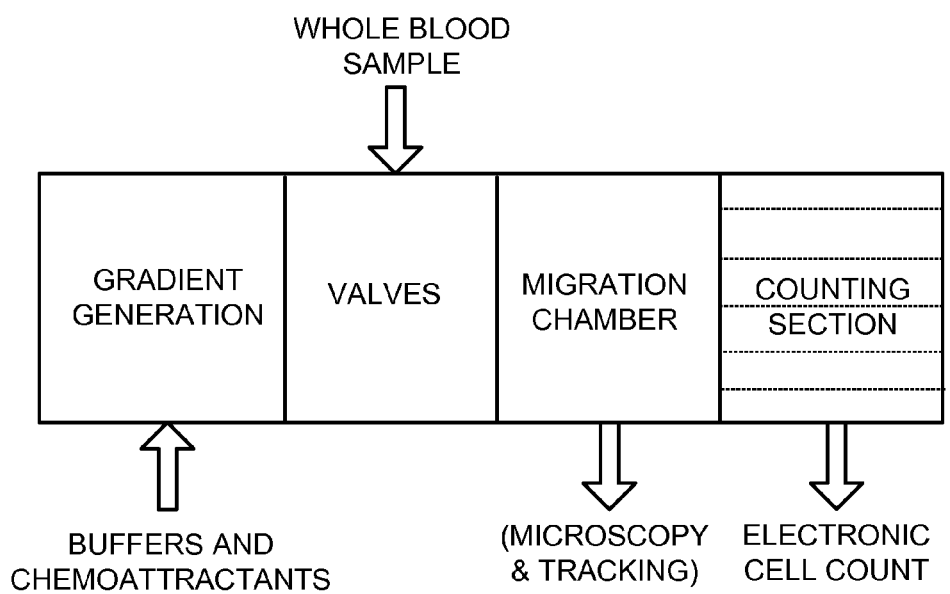
FIG. 1 is a schematic diagram of a system configured to perform quantitative analysis of migration behavior in accordance with the present invention.

A schematic depiction of a device in accordance with certain embodiments of the invention is shown in FIG. 1. In one embodiment, the device includes a migration chamber in which biological particles can be deposited and exposed to a gradient. The device may further include channels for delivering a chemical gradient to the migration chamber and/or other components for generating nonchemical gradients, e.g., thermal, electrical, light, and/or magnetic field gradients.

Embodiments of the present invention may further include pumps, fluid reservoirs, optical and/or electrical detectors, and other components configured to generate and/or measure the migration behavior of biological particles. The device depicted in FIG. 1 can be provided as a single structure or alternatively as a plurality of components that can be assembled and/or disassembled. In preferred embodiments, the migration chamber is provided as a disposable component that can be used with a single biological sample, and detection and fluid pumping components are configured to be reusable for a plurality of samples.

Figure 2A:
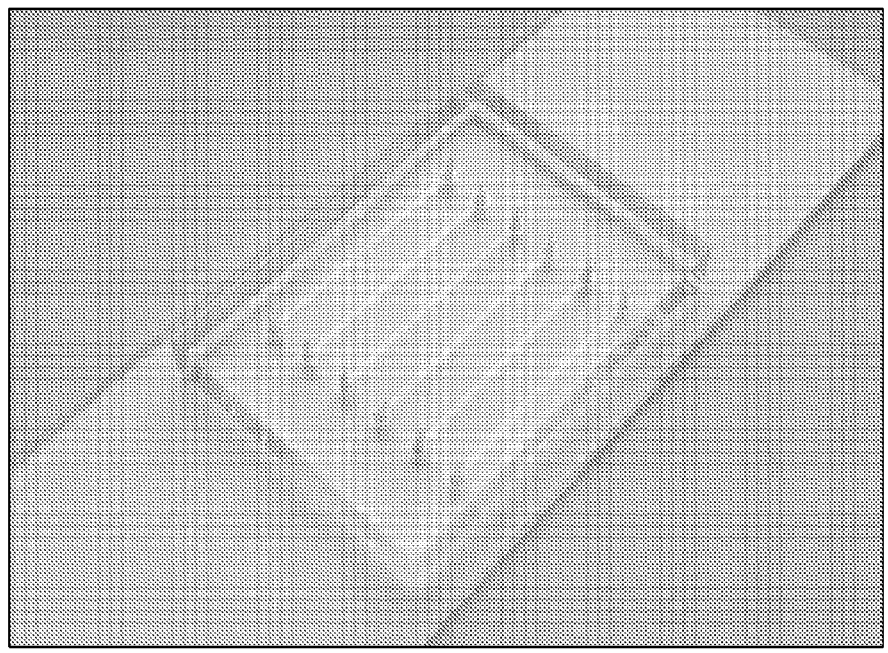
FIGS. 2A-2D are exemplary images of certain features of microfluidic devices which are configured to provide neutrophils separation from whole blood and chemotaxis assays.

The migration chamber is preferably configured so that biological particles can be directed substantially along the longitudinal direction of the migration chamber (e.g., from an inlet towards an outlet thereof) and allowed to migrate in response to one or more gradients provided in the migration chamber. For example, gradients can be formed across the width of the migration chamber, but other configurations or orientations can be provided. In certain embodiments, a plurality of such migration chambers may optionally be provided in a single system (e.g., on a single chip or substrate). A plurality of migration chambers, in the absence of a gradient source, is shown in FIG. 2A.

Figure 2B:
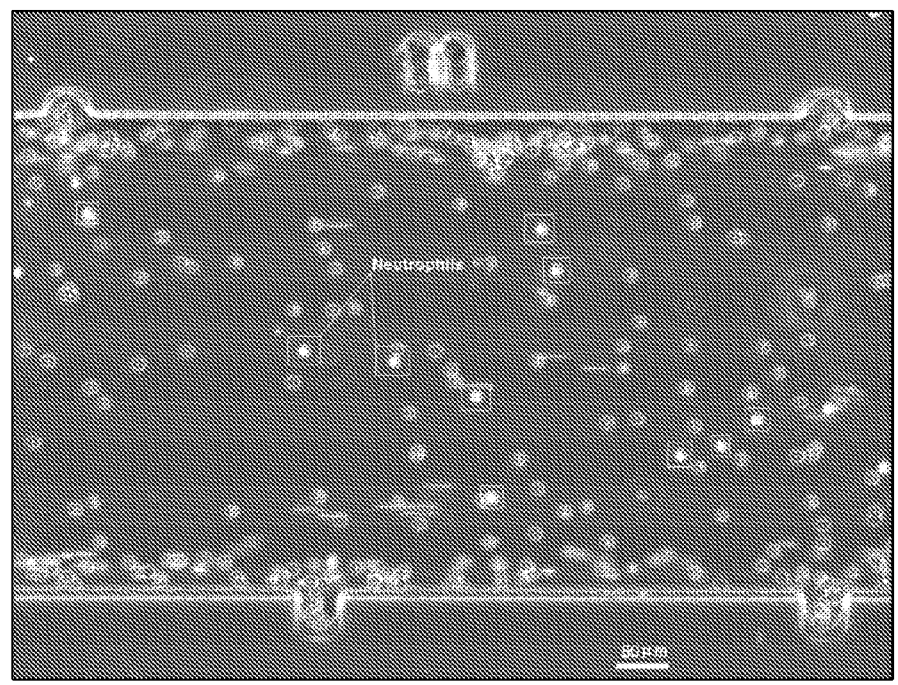
Figure 2C:
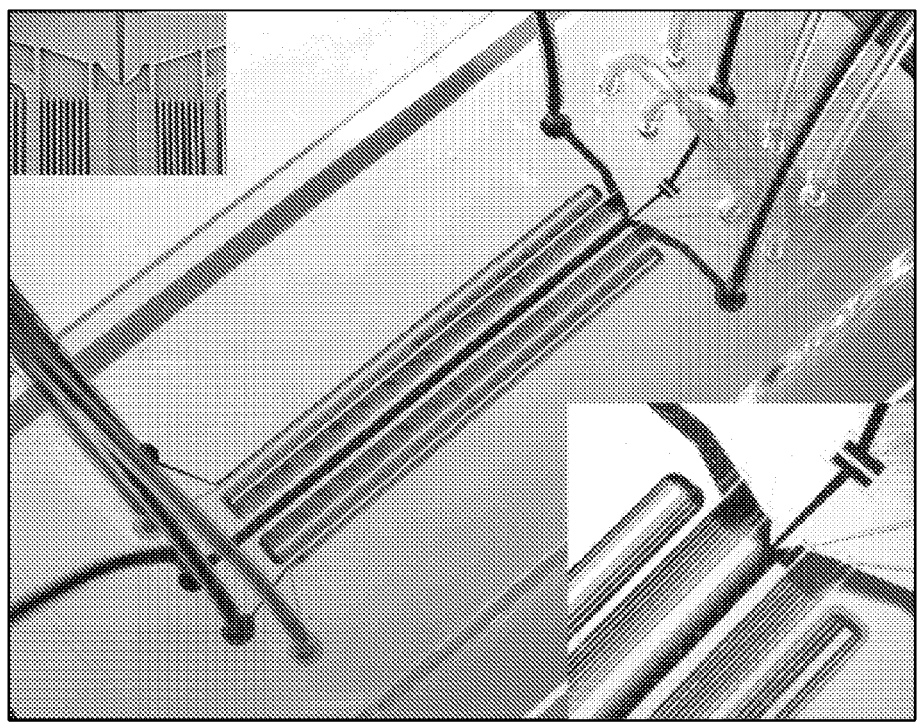
Figure 2D:
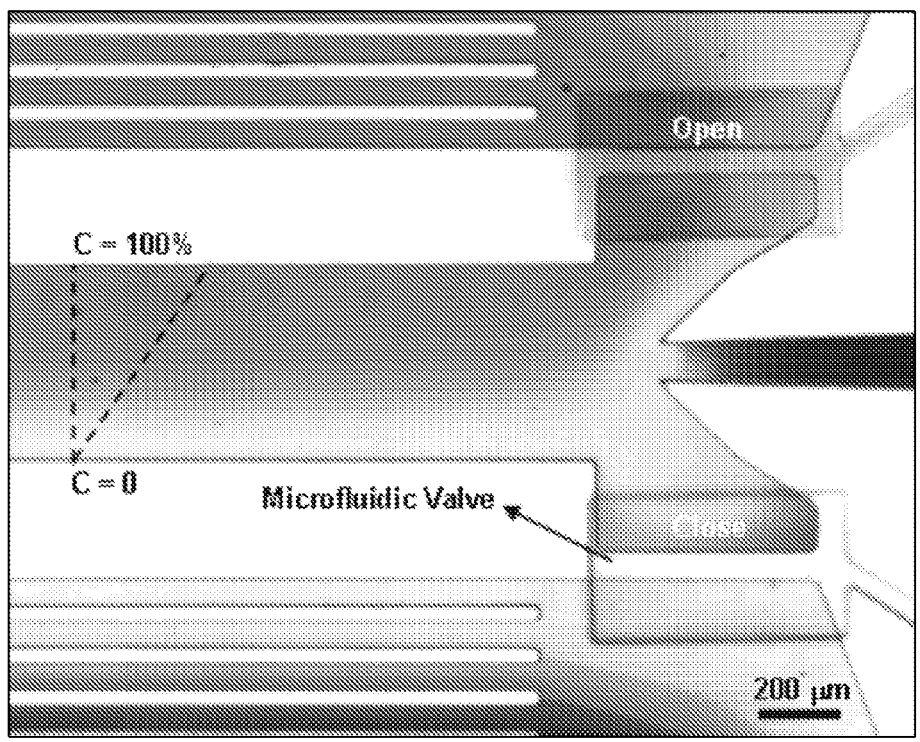

Exemplary embodiments of the invention may further include one or more gradient chambers, e.g., along a lateral side of the migration chamber. Such gradient chambers may include a plurality of inlets through which fluids of different chemical compositions and/or concentrations may be introduced. The fluids may be combined under laminar flow conditions such that they form a gradient, e.g., a step gradient or a continuous gradient. In further embodiments, other mechanisms may be employed to form gradients in the gradient chamber. For example, a chemical gradient may be formed by subjecting a fluid to electrical or magnetic forces that result in spatial distribution of components. In certain embodiments, a second gradient chamber is provided. Additional gradient chambers can provide, e.g., rapid changes in gradient conditions in the migration chamber. Gradient chambers disposed along the lateral sides of the migration chamber and separated from the migration chamber by valves are shown in FIGS. 2C and 2D. Gradients may also be formed on the device without the use of a gradient chamber. For example, the migration chamber may include a plurality of inlets through which different fluids that combine under laminar flow conditions to form a gradient may be introduced directly. Gradients may also be generated outside of the device and delivered to the migration chamber using standard fluid handling techniques.

Embodiments of the present invention can include one or more valves. Such valves can be configured to allow a controlled introduction of biological particles and/or buffers or other fluids into the migration and/or gradient chambers. For example, the biological particles may be suspended in a fluid and/or separated from a more complex solution or sample such as, e.g., a volume of whole blood, and controllably introduced into the migration chamber using a valve. Valves can also be provided to control the introduction of solutions containing one or more chemokines or substances into the one or more gradient chambers.

Exemplary embodiments of the present invention can further provide such systems and devices that are configured to perform migration analyses on very small biological samples. For example, the size of a biological sample containing a plurality of particles that can be analyzed for migration behavior may be on the order of less than about 20 µL, or less than about 10 µL. In certain embodiments, biological samples smaller than about 5 µL may also be used.

Further chambers can be provided to hold portions of the sample(s), buffers, chemoattractants, and/or other solutions or compounds. Such substances can then be introduced into the gradient chambers and/or migration chamber as desired.

Figure 3:
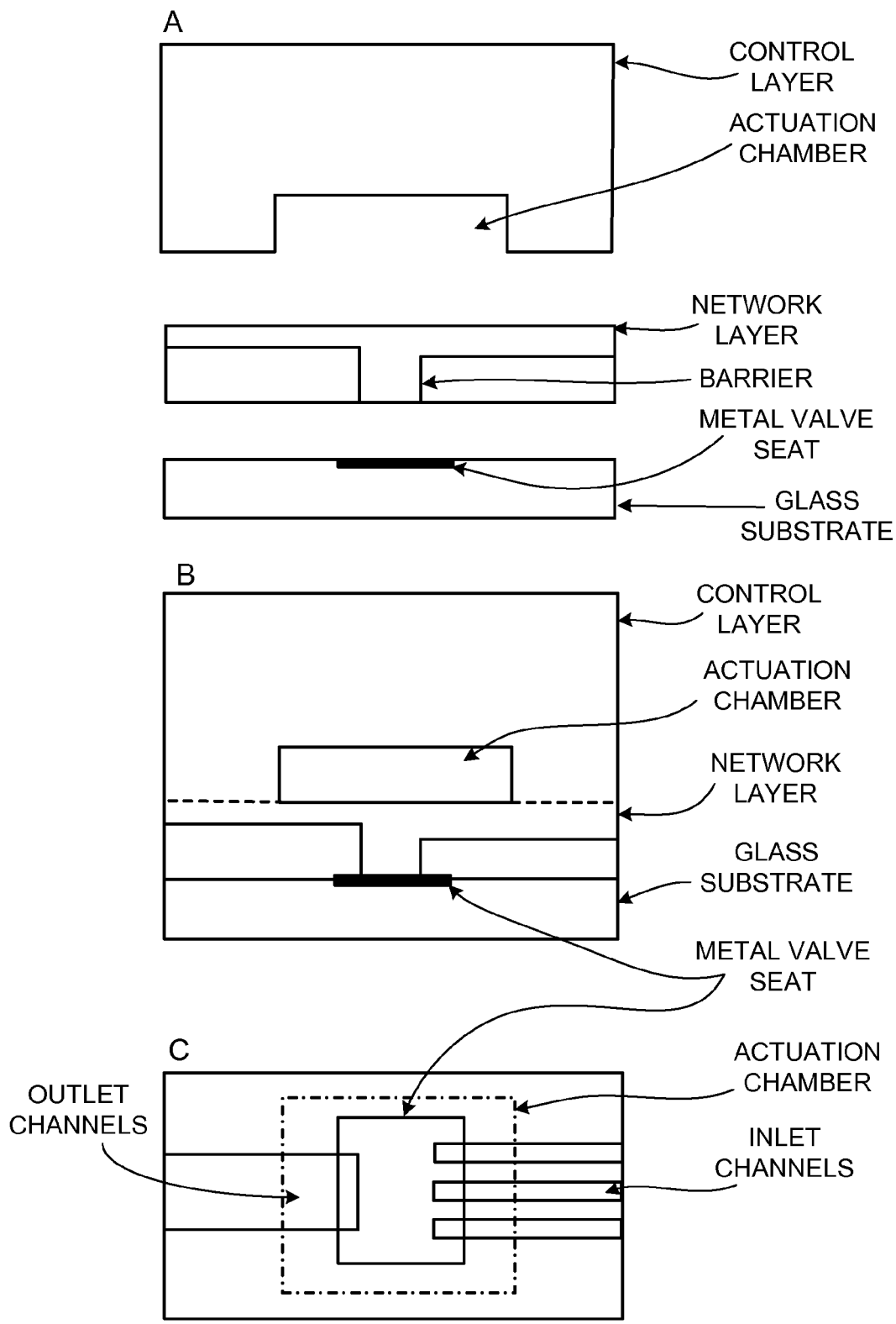
FIGS. 3A-3C are schematic illustrations of an exemplary valve that may be used to generate a gradient in exemplary embodiments of the invention.

A schematic illustration of an exemplary microfluidic valve that may be used with embodiments of the present invention is shown in FIGS. 3A-3C. Such valves can include, e.g., a valve seat on a lower substrate, a middle network layer including one or more barriers, and an upper control layer including an actuation chamber. Variation of pressure or other force within the actuation chamber can controllably move the barrier towards or away from the valve seat, thus controlling a flow of a fluid and/or particles by the barrier and through a channel or chamber. Details of the construction of such microfluidic valves and further configurations thereof are described, e.g., in. D. Irimia et al., *Lab on a Chip*, 2006, 6, 191-198 and in U.S. Application No. 60/724,453.

In the exemplary apparatus shown in FIG. 2D, the upper valve is open to pass a chemoattractant gradient from the upper gradient chamber into the migration chamber. The lower valve is closed, so that no chemoattractant is provided towards the migration chamber from the lower gradient chamber.

Inlets may also be provided in exemplary systems or devices of the present invention to facilitate introduction of the samples, solutions, etc., into the various chambers, for example, through one or more small tubes (e.g., capillary tubes). For example, syringes, needles, and the like can be used in conjunction with appropriately sized tubes (e.g., capillary tubes) to introduce various samples and solutions into the devices. Other connections between microfluidic devices and laboratory and/or clinical equipment are known in the art and may be used with certain embodiments of the present invention.

Exemplary systems or devices in accordance with the present invention may also include additional elements, e.g., for sample preparation and waste storage. For example, devices may include mechanical filters configured to remove and/or trap particles such as, e.g., red blood cells or other cells, based on their relative sizes.

Fabrication of Exemplary Systems and Devices

A variety of techniques can be employed to fabricate exemplary systems and devices in accordance with embodiments of the invention, where the particular techniques employed can be selected based in part on the materials of choice. Exemplary materials for fabricating systems and devices in accordance with embodiments of the invention include glass, silicon, steel, nickel, poly(methylmethacrylate) (PMMA), polycarbonate, polystyrene, polyethylene, polyolefins, silicones (e.g., poly(dimethylsiloxane)), and combinations thereof. Other materials that may be used with embodiments of the present invention, and methods for fabricating channels, chambers and other features in such materials, are known in the art. Fabrication methods that may be used include, for example, photolithography (e.g., stereolithography or x-ray photolithography), molding, embossing, silicon micromachining, wet or dry chemical etching, milling, diamond cutting, Lithographie Galvanoformung and Abformung (LIGA), and electroplating.

Exemplary systems and devices of the present invention may be fabricated in one or more pieces that are then assembled. Layers of a system or device may be connected or bonded together using, for example, clamps, adhesives, heat, anodic bonding, or reactions between surface groups (e.g., wafer bonding). Alternatively, a system or device that includes channels in more than one plane may be fabricated as a single piece, e.g., using stereolithography or other three-dimensional fabrication techniques.

For example, a system or device for assessing migration behavior of biological particles in accordance with embodiments of the present invention can be formed using the following exemplary procedures. First, the geometrical layout of the various chambers, channels, microfluidic valves, etc. as described herein can be prepared using design software such as, e.g., AutoCAD software (AutoCAD 2000, Autodesk Inc.). The resulting patterns can then be printed on a transparency, e.g., a Mylar mask, using a high resolution, e.g., a resolution of about 50,000 dpi (Fineline Imaging, Colorado Springs, Colo.).

The exemplary chemotaxis devices that incorporate microfluidic valves as described herein can be formed fabricated using multilayer techniques. For example, two master molds can be prepared from silicon wafers by first coating the wafers with a layer of SU8 photoresist that is approximately 50 µm thick. After exposing the SU8 photoresist to UV light through the Mylar masks in a mask aligner and developing the photoresist, features that are about, for example, 50 µm tall can be produced on top of the flat silicon wafers. Other feature heights may be produced using similar techniques as desired. These two master molds include the patterns for the microfluidic features and the valve control features, respectively.

Polydimethylsiloxane (PDMS, Dow Corning, Midland, Mich.) can then be prepared in accordance with manufacturer's instructions, and then coated on the two master molds in a thin film by spinning the coated master molds in a spinner at about 1000 rpm for about 30 seconds. The master mold containing the control structure can then be placed in a larger Petri Dish and covered with a further layer of PDMS that is about 4 mm thick for stability. The PDMS may then be cured by placing the two master mold wafers overnight in an oven set at 65° C. The thicker PDMS layer containing the control structures can be removed from the corresponding master mold, cut to size, and holes of an appropriate size punched through the PDMS to communicate with the actuation chambers using a sharpened needle (Small Parts, Miami Lakes, Fla.). The thicker PDMS layer and the wafer with the thin PDMS film may then be treated with oxygen plasma (March, Concord, Calif.), aligned and bonded together on a 75° C. hot plate.

After bonding, the bonded PDMS layers can be removed from the wafer and cut again to size. Further holes may then be punched through the two layers of PDMS to provide inlet and outlet channels in communication with the various chambers. The two-layer PDMS construct can then be exposed to an oxygen plasma and bonded onto a glass slide (Fisher Scientific, Pittsburgh, Pa.) for structural stability. During this bonding procedure, a vacuum can be applied to the microfluidic valves using syringe and tubing connections to maintain them in an open position, thereby preventing them from irreversibly bonding to the glass substrate. Further details of this exemplary fabrication and assembly procedure are described, e.g., in D. Irimia et al., Lab on a Chip, 2006, 6, 191-198.

Gradients

Systems and devices in accordance with embodiments of the invention may also allow observation (e.g., direct optical) of migration behavior of biological particles in response to gradients, e.g., chemical and nonchemical gradients (e.g., thermal, electrical, light, and/or magnetic field gradients). The shapes and compositions of such gradients can be selected to affect migration of the desired particles. In certain embodiments, the gradient employed in the device is not solely a gradient in fluid velocity, pressure, or shear force.

In certain embodiments, the gradient may be a chemical gradient. Exemplary compounds that may be used to generate chemical gradients can include chemokines or other compounds capable of inducing migration of various particles that are known in the art. Various concentration gradients of a chemoattractant or other substance can be provided across the migration chamber (e.g., substantially perpendicular to the direction of flow). The gradient may be controlled based on the selection of source concentrations introduced into a gradient chamber, such as that depicted in FIG. 2D, and the particular configuration of such gradient chambers. For example, such gradient chambers can be configured to generate a substantially linear gradient (e.g., one that varies uniformly from 0% to 100% concentration) across the migration chamber when the configuration is maintained in an approximately steady-state condition. Nonlinear and step gradients may also be employed in further embodiments of the invention. Further details of such exemplary gradient chambers are described, e.g., in Irimia D. et al., Universal Microfluidic Gradient Generator, *Analytical Chemistry* 2006, 78, 3472-3477.

Gradients of two or more substances can be provided in sequence, e.g., by introducing particular concentrations of each substance into two gradient chambers, as shown in the exemplary configuration of FIG. 2D. A particular gradient can be selected by actuation of valves associated with the corresponding gradient chamber. For example, with an upper valve opened and a bottom valve closed, particles in the migration chamber can be exposed to the chemical gradient from the top gradient chamber. By simultaneously closing the upper valve and opening the bottom valve, particles may then be exposed to the gradient from the bottom gradient chamber.

Multiple compounds or other substances may be present in the same fluid, and a single fluid may provide gradients of multiple chemical species. For example, gradients of two or more substances can each increase in the same lateral direction, or they may increase in opposite directions. (For example, one substance increases from 10% to 50% along one lateral direction, while a second substance B increases from 0% to 50% in the opposite direction across the migration chamber.)

FIG. 2C is a photograph of an exemplary device that includes valve arrangements, a migration chamber running from the upper right to lower left portion of the figure, and gradient chambers provided along the lateral sides of the migration chamber. A plurality of tubes configured to supply and withdraw biological samples, buffer solutions, and chemoattractants to and from the migration and/or gradient chambers are also shown. The inset image in the upper left corner of FIG. 2C shows a close-up view of a portion of a gradient chamber and associated microfluidic valve. The inset image in the lower right corner of FIG. 2C shows a close-up view of the proximal portion of the gradient chambers, migration chamber, and associated valves.

In addition to spatial gradients, exemplary embodiments of the present invention may also employ temporal gradients. For example, a gradient may be constant over time, or the composition or shape of the gradient may vary over time. Transient gradients along the migration chamber can be provided, e.g., by opening and/or closing one or more valves between gradient chambers and a migration chamber at particular times during processing or analysis of a biological sample. Such times can be determined, e.g., based on the dimensions of the migration and gradient chambers, the flow rates through such chambers, the initial concentrations of substances introduced into the gradient chambers, and diffusivities of the various components within the migration chamber.

Further embodiments of the present invention may be used to study photomigration effects. For example, systems and devices as described herein may be provided with a graduated filter having a varying degree of transmissivity, e.g., above and/or below the migration chamber. Such a filter can be printed on a transparency and affixed to an outer surface of the apparatus such that it partially blocks light from reaching at least a portion of the migration chamber. Preferably, the filter can be configured to provide a gradient of light intensity that is substantially the same across each lateral cross-section of the migration chamber. The gradient profile can be linear or non-linear. An external light source of a particular intensity can be directed at the migration chamber such that it first passes through the filter to generate the gradient of light intensity within the migration chamber.

Particle Detection

Systems and devices provided in accordance with embodiments of the invention can include one or more detection arrangements configured to quantify and/or characterize the migration behavior of particles. Such detection arrangements can be based on, e.g., optical or electrical detection techniques. Detection of biological particles may be qualitative and/or quantitative.

For example, a detection arrangement may employ optical techniques, e.g., visual inspection or image detection, such as those used in conventional microscopic particle detection systems. Such optical techniques may be used to observe positions and/or visible characteristics of unmodified particles or particles that have been labeled with stains, including surface and/or interior stains. Optical detection techniques may also be employed to differentiate between types of cells that may be present in the migration chamber, e.g., via size, shape, morphology, and/or labeling characteristics. Electrical detection of particles may also be employed, e.g., using a Coulter counter or similar apparatus. Detection may occur while cells are migrating in the device and/or after such migration has been completed. The detected biological particles may or may not be viable while being detected.

Particles may be detected in the migration chamber and/or they may be removed from the migration chamber for detection. For example, lateral migration of biological particles may be observed directly in the left portion of the migration chamber shown in FIG. 4 using, e.g., optical, microscopy, and/or digital imaging techniques. After such migration has occurred for a particular time interval, the migrated particles can be released from the surfaces of the migration chamber using, e.g., a flow of isotonic buffer or other fluid through the migration chamber. The lateral distribution of biological particles (e.g., neutrophils), which occurs as a result of a gradient in the migration chamber, can then be determined based on the numbers of biological particles detected by a detection arrangement provided along the width of a distal portion of the migration chamber.

Figure 4:
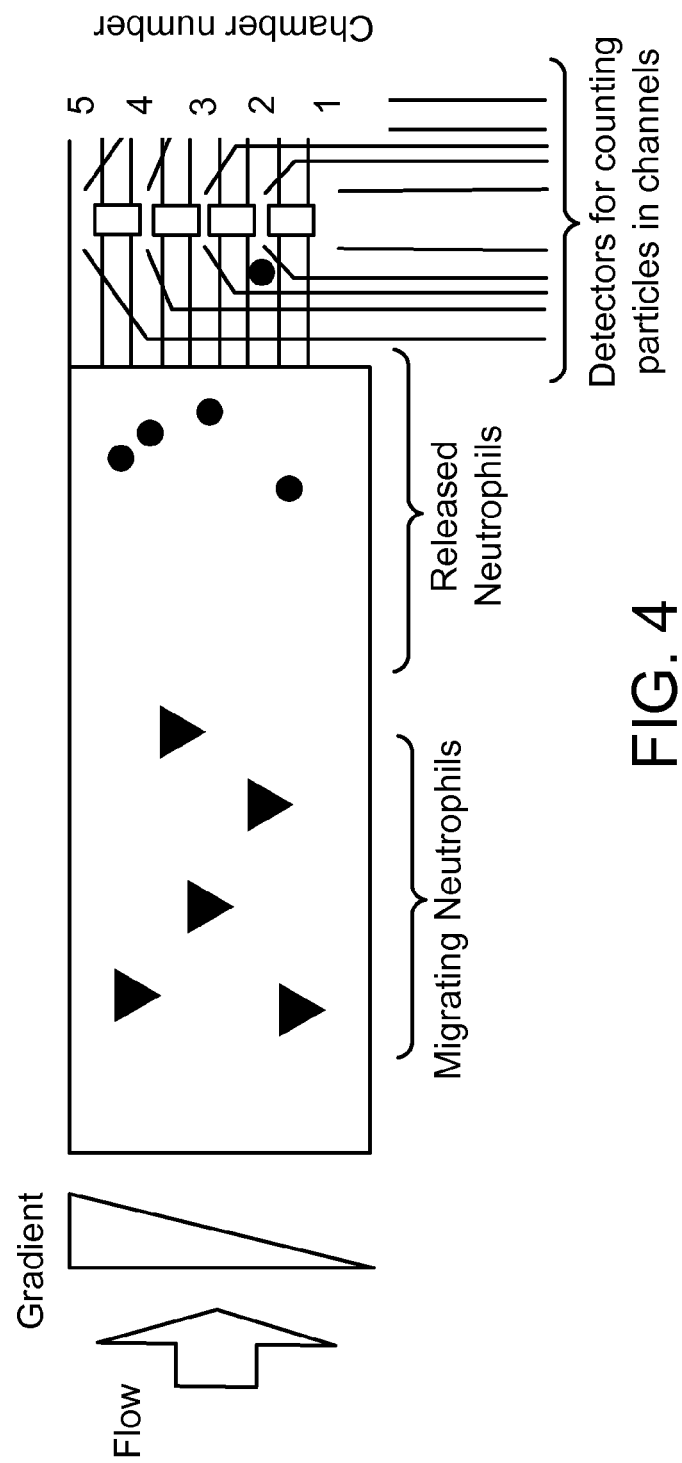
FIG. 4 is a schematic diagram of an exemplary system that includes a detection arrangement having a plurality of detectors.

An exemplary detection arrangement provided at the distal (e.g., downstream) portion of the migration chamber is shown in FIG. 4. The detection arrangement may include a plurality of detectors, e.g., sensors or other detection devices, arranged across the width of the migration chamber. The detectors can include, for example, optical detectors (e.g., LEDs and photodetectors) or electrical detectors that are configured to detect particles based on impedance or inductance. In certain embodiments, each such detector may be coupled to one of a plurality of channels through which particles can pass and be counted. Other line detection techniques may also be employed with the detection arrangement. Such line techniques include raster scanning and CCD or other optical arrays.

The ends of walls separating the plurality of channels may be shaped to deflect particles into one of the channels to be detected. The number of such channels can be selected based on, e.g., the width of the migration chamber and the sizes of the biological particles being processed. For example, the width of the counting channels can be configured to be slightly larger than a maximum diameter of the biological particles. A single detector can be associated with each counting channel, such that any biological particle passing through a counting channel will be identified by the detector associated with that channel.

The detectors can be provided in communication with a conventional processing arrangement and/or a memory arrangement such as, e.g., a personal computer, workstation, or personal digital assistant (PDA). This configuration can allow the number and lateral positions of the biological particles from the migration chamber to be determined and saved and/or processed mathematically to produce a distribution of particles.

Portions of the migration chamber can be transparent or configured to allow sufficient light to pass to allow direct observation of biological particles using, e.g., optical microscopy. Such direct observation can provide further data characterizing the response of the biological particles to various gradients, including transient responses.

Surface Functionalization

Surfaces of exemplary systems and devices of the present invention may be functionalized, e.g., to capture certain biological particles and/or to prevent or inhibit nonspecific adsorption. Compounds that may be used to functionalize surfaces to reduce nonspecific adsorption of compounds and cells are known in the art and can include, e.g., polyethylene glycol and bovine serum albumin. Binding moieties for biological particles may also be used to functionalize surfaces, and a particular binding moiety employed can be selected based on the type of cell or particle to be captured.

Examples of binding moieties include antibodies, aptamers, and cell adhesion molecules (CAMs). Other binding moieties can include, e.g., carbohydrate-binding proteins (including antibodies) capable of interacting with glycoproteins and glycolipids present on the surface of the biological particles. Examples of carbohydrate-binding proteins include P-selectin, L-selectin, mel-14, and hemagglutinins. Glycoproteins that may be present on certain biological particle surfaces, and to which carbohydrate-binding proteins could bind include, e.g., sialyl Lewis X, discoidin (Dictyostelium), bindin, ZP1-3 (ovocyte), aminohexyl sugars and N-acetylglucosamine lipids (against carbohydrates on hepatocyte surface), and gangliosides (against nerve cells). For example, binding moieties that may be used with exemplary embodiments of the present invention are described, e.g., in Brandley B K and Schnaar R L: Cell-Surface Carbohydrates In Cell Recognition And Response, Journal of Leukocyte Biology, 1986, 40(1), 97-111, and in Bovin N V and Gabius H J: Polymer-immobilized carbohydrate ligands: Versatile chemical tools for biochemistry and medical sciences, Chemical Society Reviews 1995, 24(6), 413-421.

Binding moieties used in exemplary embodiments of the invention may preferably provide for capture of a particle from a sample, where the strength of the bond with the moiety can allow subsequent migration of the captured particle along the functionalized surfaces.

The surface of the migration chamber can be modified by physical absorption of an adhesion substance. For example, neutrophils can be captured from whole blood if the surface of the migration chamber is coated or loaded with adhesion substances, including but not limited to selectins (e.g., P-selectin or E-selectin) and/or fibronectin. In certain embodiments, the binding moiety is not solely E-selectin. Other methods of adhering binding moieties to surfaces, e.g., via chemical bonding, are known in the art.

Such capture and migration assays can provide an approximation to in vivo conditions, where neutrophils may roll on endothelial surfaces, stick to the endothelium in regions of higher selectin expression, and respond to gradient of chemokines such as IL-8 and migrate into tissues. Consequently, exemplary embodiments of the present invention can be used to gain further insight into certain in vivo behaviors of neutrophils.

Methods

Exemplary systems and devices of the present invention may be employed to observe the migration behavior of particles, e.g., in response to gradients. For example, a solution containing such particles can be introduced into a migration chamber, and some or all of the particles may then bind to a binding moiety provided on a surface of the chamber. A gradient can then be established in the migration chamber, and the effect of the gradient on the particle locations and/or morphologies may then be observed or otherwise detected. In further embodiments, particles can be introduced into the migration chamber and exposed to a gradient (e.g., of temperature, light, electrical potential, or magnetism), while passing through the migration chamber. The residence time over which such migration occurs can be controlled by regulating the flow rate of the solution containing biological particles through the migration chamber. The particular gradient used can be selected based on the nature of the particles being observed and the particular behavior to be studied.

Many comparative assays can be performed using samples taken from a single patient over any desired timeframe because of the very small size of the samples. Such comparative assays can be performed to assess the effects on migration of, e.g., different gradients of chemokines, different combinations of chemokines, or chemotaxis modifying drugs (e.g. chemotaxis inhibitors) that can be introduced into the migration chamber. Compounds that may be used to generate gradients that can affect migration of neutrophils include ELR-positive CXC chemokines such as interleukin-8 (IL-8), leukotriene B4, zymosan-activated serum, and N-formylated peptides (e.g., N-formyl-methionyl-leucyl-phenylalanine (fMLP)). In certain embodiments, the compound is not solely fMLP. C5a can attract both neutrophils and monocytes, and SDF1 is a chemoattractant for lymphocytes. Other chemokines include CC chemokines, CXC chemokines, C chemokines, and CX3C chemokines. CC chemokines that induce the migration of monocytes and other cell types such as NK cells and dendritic cells. Examples of CC chemokines are monocyte chemoattractant protein-1 (MCP-1 or CCL2); CCL28, which attracts lymphocytes (e.g., T cells and B cells that express CCR10) and eosinophils that express CCR3; and CCL5 (or RANTES), which attracts T cells, eosinophils and basophils that express the receptor CCR5. An exemplary CXC chemokine is CXCL13 that attracts for lymphocytes. Examples of C chemokines include XCL1 (lymphotactin-α) and XCL2 (lymphotactin-β), which attract T cell precursors. An exemplary CX3C chemokine is fractalkine. Other specific compounds are known in the art.

In further embodiments of the invention, biological particles may be exposed to multiple gradients. For example, gradients of two chemokines, or two gradients each employing the same chemokine but with one gradient further including another compound, can be employed. Switching between gradients and observing or measuring the resultant migration behavior can provide, e.g., information relating to the functional status of the particles.

Detection of cells or other biological particles can be performed within the migration chamber or outside the migration chamber, e.g., using one or more detection arrangements as described herein. For example, such detection can be performed outside of the migration chamber by flushing or otherwise transporting particles from the migration chamber, e.g., in response to a flow provided through the migration channel when particles do not adhere to the channel surface. Alternatively, such flushing may be achieved by increasing the shear stress on the particles or introducing a substance (or other condition) that facilitates release of the particles from the surfaces, e.g., by chemical degradation of a bond between the particle and a binding moiety or between a binding moiety and a surface of the migration chamber. Bonds between a binding moiety and the surface of a migration chamber may be chemically labile (e.g., to a change in pH, salt concentration, or enzymatically), electrochemically labile (e.g., a bond that may be oxidized or reduced), or photolabile (e.g., a bond that is photochemically cleaved).

Figure 5:
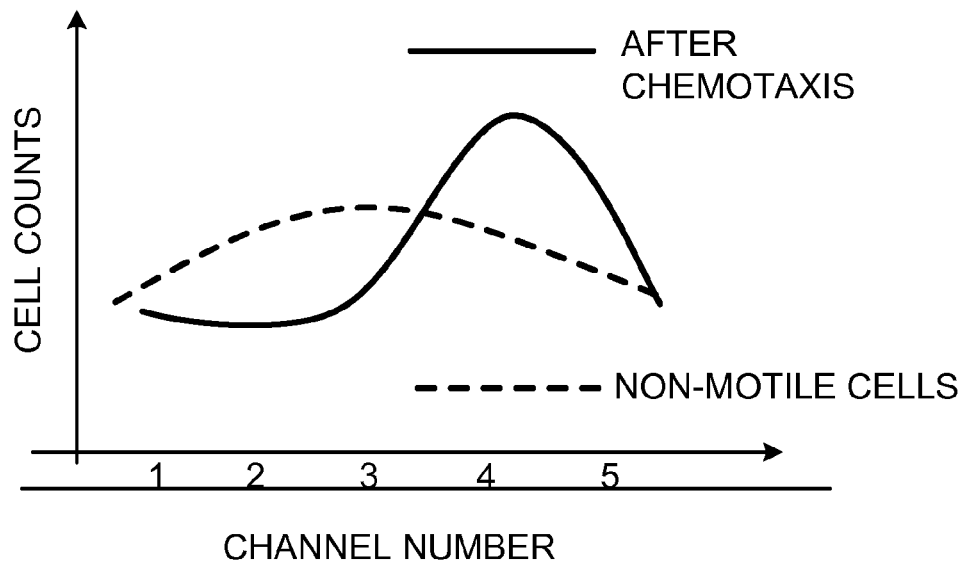
FIG. 5 is a graph showing predicted distributions of motile and non-motile cells after being subjected to a chemical gradient.

Exemplary population distributions of biological particles (e.g., cells) that may be obtained using the device of FIG. 4 are shown in FIG. 5. For example, non-motile cells that are relatively unaffected by a particular gradients exhibit an approximately symmetrical distribution across the width of the migration chamber (represented by a dashed line). The population is largest near the center of the migration channel (e.g., in channel 3) because particles are introduced predominantly near the center of the migration chamber under pressure-driven flow, as shown in the exemplary apparatus of FIG. 2D. An exemplary distribution of cells that exhibit chemotaxis in the provided gradient (represented by a solid line) is skewed towards the side of the migration chamber having a higher concentration of a chemoattractant (e.g., channels 4 and 5).

Rapid analysis of migration of neutrophils in response to certain chemoattractants, e.g., such as interleukin-8 (IL-8, Catalog #208-IL, R&D Systems inc.) or N-formyl-methionyl-leucyl-phenylalanine (fMLP, Part # F3506, Sigma-Aldrich) can be performed using exemplary embodiments of the present invention. Such studies can be performed using very small biological samples, e.g., on the order of tens of microliters or less. For example, an assay of neutrophil migration under a gradient can be performed in less than about 15 minutes using a sample of less than about 10 µl of whole blood, or less than about 5 µl of blood. Such rapid assays can provide information on behavior of 'fresh' viable neutrophils. Short time intervals allow for assessing the activation/inhibition status of neutrophils from the blood of patients, particularly patients using medications that can inhibit neutrophil migration. The effects of such medications can be lost using conventional assay techniques that include, e.g., repeated washing of neutrophils in buffers during centrifugation protocols.

Activity of neutrophils may be assessed in conjunction with medical management of many conditions. Devices and methods of the invention can be used to assay for drugs having the desired effect on neutrophils for a particular condition. Devices and methods may also be employed in clinical diagnosis or monitoring of a condition. Diseases where it may be desirable to suppress the activity of neutrophils include, for example: ischemia-reperfusion injury (e.g., ischemic stroke, myocardial infarction, and kidney ischemia reperfusion after transplant/trauma/blood loss); sterile inflammation due to neutrophil infiltration; severe asthma; colitis (e.g., in inflammatory bowel disease); periodontitis; retinopathy; and bone marrow transplant (e.g., monitoring graft versus host disease). Diseases and conditions where the activity of neutrophils is reduced and enhancement of their activity may be desirable include: neonatal infections; infections in older patients; during chemotherapy; during long term, nonspecific immunosuppressive treatment (e.g., arthritis, post-transplantation); sepsis; burn injury; and clozepine treatment.

Chemotaxis assays for other cells may also be performed using exemplary embodiments of the present invention. The devices and methods may be used to screen for drugs that affect migration behavior in the following conditions: cancer cell migration and metastasis; scar formation from fibroblast and monocyte migration, e.g., from burns and surgical wounds; formation of new blood vessels or the repair of existing vessels effected by endothelial cells; skin allergies and hyper-sensitivity, where the migration of dendritic cells from the skin into the lymph nodes plays a critical role in the activation of immune response.

Samples

Various samples that include biological particles may be employed with the exemplary systems, devices and methods of the present invention described herein. Such samples may be obtained from a subject, e.g., blood, lymph, ascites, semen, saliva, urine, and cerebrospinal fluid. Other sources of samples can include environmental samples and cultures. Samples may be used directly as obtained from a source, or they may be subjected to sample preparation procedures. Such procedures include addition of preservatives (e.g., anticoagulants), dilution, labeling, and depletion of undesired populations (e.g., red blood cell lysis). Sample preparation may occur within the exemplary systems and devices described herein, or prior to introduction of the sample into these systems and devices.

For example, samples of whole blood may be employed for analysis of neutrophil migration. Anticoagulants may be added to such samples such as, e.g., heparin, P-PACK, and/or EDTA. Heparin may interfere with capture of neutrophils on surfaces containing selectins. In further embodiments, blood samples can be used with no added anticoagulant, particularly when performing a rapid analysis (e.g., within about 10 minutes after drawing the blood sample, which can be prior to formation of a coagulation cascade).

As discussed, the systems, devices, and methods of the invention may be employed with small samples, e.g., less than about 1 mL, 500 µL, 100 µL, 50 µL, 20 µL, 10 µL, or 5 µL. As will be understand by one skilled in the art, a minimum volume, e.g., at least 0.5 or 1 µL, may be required to obtain sufficient biological particles for analysis. The actual sample volume employed will depend on the nature of the sample and the identity of the biological particle.

The invention is further described in the following, non-limiting examples.

EXAMPLES

To closely mimic the in vivo scenarios existing around cells, a simple and efficient in vitro chemotaxis study demands two essential steps: (1) the isolation and immobilization of neutrophils on the device for subsequent microscopy and monitoring cellular responses and (2) the ability to create a dynamic yet controlled and complex environment of multiple chemokines around the cells. Here, a technique is presented that integrates the two major steps of isolating neutrophils from whole blood samples and probing their migration, on a single microfluidic platform which is also capable of performing fast switches between multiple chemokines gradients. This device requires just a drop of whole blood easily obtained from a finger prick (5-10 µL) and directly isolates primary neutrophils into the cell capture and migration chamber coated with cell adhesion molecules (CAM). The surface modification protocol has been optimized for efficient neutrophil isolation and studied neutrophil migration under gradients of different chemoattractants. The procedure provides a quick and integrated platform to perform the entire migration study in vitro within a single microfluidic device in a bio-mimetic scenario.

Fabrication

Designs of devices were prepared using AutoCAD software (AutoCAD 2000, Autodesk Inc.) after which they were printed on a transparency at resolution of 50 000 dpi (Fineline Imaging, Colorado Springs, Colo.). Two designs were used, one for optimizing the efficiency of neutrophil capture from whole blood and the other for integrated capture and chemotactic assays, as shown in FIGS. 2A-2D. The first design is for a capture device consisting of simple channels with markings on the side for positional information and fabricated using standard microfluidic technologies (FIG. 2B). The second design incorporates microstructured valves and was fabricated using multilayer procedures. For this, two silicon masters were prepared using SU8 soft photolithography techniques. Polydimethylsiloxane (PDMS) was patterned on the two wafers to replicate the microfluidic network in a 150 µm thin layer and the control network in a 4 mm thick layer. Devices were fabricated by the bonding of the control PDMS layer on top of the microfluidic network layer and the two layers on a glass slide as described in D. Irimia et al., *Lab on a Chip,* 2006, 6, 191-198 and U.S. Application No. 60/724, 453. During bonding, vacuum was applied to the valves using syringe and tubing connections to maintain them in open position and prevent them from irreversibly bonding to the glass substrate. Appropriate inlet and outlet ports were punched using sharpened needles (Part # NE-201PL-C, Small Parts Inc., Miramar, Fla.) before bonding the devices to glass slides. The channel dimensions of the neutrophil capture chambers were 450 µm wide and 80 µm tall.

Cell Adhesion Molecules and Surface Treatment

Three different adhesion molecules (P-selectin, E-selectin and fibronectin) were used to capture primary neutrophils from whole blood in the microfluidic channels. These substrates were chosen because of their significant role in neutrophil trafficking in vivo. To characterize the neutrophil capture efficiency, the cell capture chambers were coated with the adhesion molecules by flowing through solutions of six different concentrations of each adhesion molecule (concentrations shown in Table 1). Solutions were prepared by diluting the stock solution in sterile water or phosphate buffered saline (PBS) as advised by the vendors. These dilutions were loaded in the six cell capture chambers of the device and incubated for 1 h at room temperature. After one hour, P-selectin was aspirated and the flow chambers perfused with 2% HSA (Human Serum Albumin, Sigma-Aldrich Catalog # A5843) in Hank's buffer saline solution (HBSS, Sigma-Aldrich Catalog # H9269) to block non-specific binding sites and incubated for at least 15 minutes.

TABLE 1

Concentration of the solutions used for surface treatment and neutrophil isolation in microfluidic channels

| Substrate | Conc. (µg/mL) | Vendor | Catalog # |
|---|---|---|---|
| Human recombinant P-selectin | 0.1, 10, 25, 50, 75, and 100 | R&D Systems Inc. | ADP3-050 |
| Human recombinant E-selectin | 0.1, 1, 10, 25, 50, and 100 | R&D Systems Inc. | ADP1-050 |
| Fibronectin | 1, 10, 50, 100, 300 and 500 | R&D Systems Inc. | F0895 |

Experimental Setup

These microfluidic flow channels, in this example, require subtle connections with the macroscopic components such as tubing, needles, syringes etc. Therefore, to ensure sealed connections, tubing and needle specifications are chosen such that the inside diameter (ID) of the tubing is slightly smaller than the outside diameter (OD) of the connecting needle, while the OD of the tubing is slightly larger than the ID of the punching needle used previously to make inlet/outlet ports in the PDMS device. This setup has been well standardized and is consistently employed for all the experiments performed in this study.

Characterization of Neutrophil Capture

The PDMS device used to characterize cell capture consists of six distinct parallel channels each having an inlet and an outlet port (FIG. 2A). The channel dimensions of each segment of the capture device are 750×450×80 µm (L×W×H). The length of each segment was chosen such that it will conveniently fit in the field of view at 10× ocular and 10× objective magnification. 10 µL whole blood was mixed with 70 µL it heparinized HBSS solution and loaded in the cell chamber. Six 1 mL syringes (Part #309602, Becton, Dickinson and Company, Franklin Lakes, N.J.) were filled with HBSS containing 0.2% HSA. Most of the air trapped in the dead volume of the syringe was eliminated by tapping the inverted syringes. Syringes were then connected to tygon tubing approximately 10 to 12 inches long (Part # TGY-010-C, Small parts Inc.) through the needles (Part # NE-301PLC, Small parts Inc.). The syringes were placed on the syringe pump rack (PHD 2000, Harvard Apparatus, Holliston, Mass.), and the loose ends of the tubing were connected to the inlets of the device properly secured on the microscope stage. Smaller fragments of tubing were connected to the outlet ports. The pump was turned on at the rate of 4-5 µL/min, and the outlet tubings were clamped once the channels were filled with fluid, while leaving the pump running. This priming step was necessary to eliminate any trapped air pockets by continuing the inflow that pressurizes the air bubbles to diffuse through the porous PDMS matrix. Blood sample could be loaded as soon as all the air pockets were eliminated.

Neutrophil Migration Setup

The gradient generating device used to study cell migration consists of two inlets, one outlet, and a cell loading port. In a similar manner as explained above, the device was primed after functionalizing the channel surface with adhesion molecules. Two syringes were prepared, one with only buffer containing 0.2% HSA while the other also containing the appropriate concentration of chemokine. Two chemoattractants, either recombinant human interleukin-8 (IL8, Catalog #208-IL, R&D Systems inc.) or N-formyl-methionyl-leucyl-phenylalanine (fMLP, Part # F3506, Sigma-Aldrich) were employed at 10 nM and 20 nM concentrations. For consistency, the two syringes were connected to the device such that chemokine gradient in the cell capture and migration chambers was always in the same orientation, from top (100%) to bottom (0%). After the device was primed, inlet ports were clamped, and the blood sample was loaded through the cell loading port as described in the following section.

Sample Loading and Neutrophil Capture

A 1.25 mm lancet (Part #366579, Becton Dickinson) was used to prick a finger of a subject, and 10 µL whole blood was drawn with a pipette. Before withdrawing the blood, 70 µL of HBSS mixed with sodium heparin (Part #367871, Becton Dickinson) was injected into the open end of a loading needle using a pipette. The blood in the pipette was then directly mixed with the heparin solution inside the needle. A slight pressure was gradually applied to the open end of the needle using an index finger to push the blood sample through the tubing until a small drop of fluid appeared on the other end of the tubing. To avoid entrapment of air bubbles while connecting the tubing to the PDMS device, a drop of HBSS was always present in excess at the connecting ports of the device. The loose end of the sample tubing was held with forceps and carefully inserted in the PDMS port. Once a sealed connection was established, pressure was again applied to the loading needle to push samples through the cell capture and migration chamber. The inlet and outlet tubings were then clamped using binder clips for 5-10 minutes allowing cells to interact and bind with the glycoprotein molecules.

Microscopy

For the neutrophil capture characterization experiments, images for 7-10 sections (each 750 µm long, FIG. 2B) were acquired at 2 s interval using time lapse microscopy and at least 10 frames were captured. This was done to make sure that only adherent neutrophils were counted. An inverted Olympus microscope (Model # CKX41) and a CMOS color camera (Pixelink PLA742) were used to capture time lapse images in phase contrast mode. A 10× ocular and 10× objective magnification were used. The neutrophils captured in the chambers were counted manually in 7-10 distinct areas for each concentration. The average number of captured cells was calculated from three repeated experiments for each concentration and CAM. Captured time lapse images were converted to 8 bit and individual cells were tracked using Metamorph imaging software (Ver 4.1, Universal Imaging Corporation). Elapsed time and migration distance from the origin in the Y direction were derived for each cell and average displacements were calculated for the entire cell population in consideration. Migration curves representing the average distance traveled in the direction of increasing chemokine concentration against time were plotted and compared. It is notable that the slope of gradient along the flow path in the cell chamber gradually changes depending on the flow rates and the diffusivities of chemoattractants. Therefore, to maintain consistency, only the first upstream quarter of the cell chamber was considered for microscopic observation where the variations in gradient profile are minimal.

Data Analysis

To analyze neutrophil migration, mean-squared displacements of individual neutrophils were calculated $$\langle \delta(\tau)^2 \rangle$$

from the displacement of the cell during a time interval s at different time instances t, $$\delta(\tau) = |\vec{r}(t+\tau) - \vec{r}(t)|$$

SigmaPlot software (Systat software, Inc) was used to calculate $\mu$, the random motility coefficient, and P, the directional persistence time. Considering the two-dimensional migration of neutrophils on a flat surface, the following equation was used to fit a persistent random walk model for cell migration to the recorded displacement data:

$$\langle \delta(\tau)^2 \rangle = 4\mu(t - P(1 - e^{-t/P}))$$

Average random motility coefficient and average directional persistence time were calculated for at least 15 neutrophils moving on each of the surfaces coated with different substrates at optimal concentration.

Statistical Analysis

All values were expressed as average number of cells captured per square millimeter of the cell capture chamber surface area. A two-way ANOVA test was used for statistical comparisons of capture efficiencies for different substrates. Statistical significance was assigned where $P<0.05$.

Results

A microfluidic device capable of isolating neutrophils from a droplet of whole blood and performing complex in vitro chemotaxis assays was designed and tested. The effect on neutrophil capture and neutrophil chemotaxis of three different cell adhesion molecules (CAM) surface coatings and two chemoattractant gradients were compared.

Effect of Surface Treatment on Neutrophil Capture

Figure 6A:
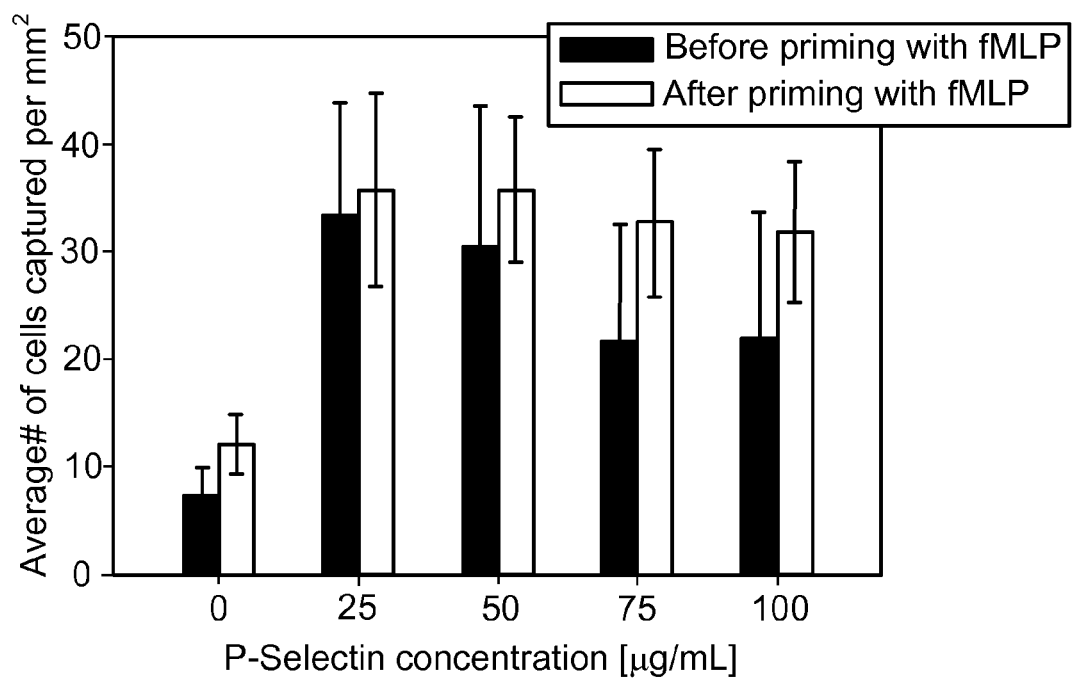
FIGS. 6A-6C are exemplary graphs indicating the neutrophil capture efficiency of surfaces treated with various concentrations of P-selectin, E-selectin, and fibronectin.
Figure 6B:
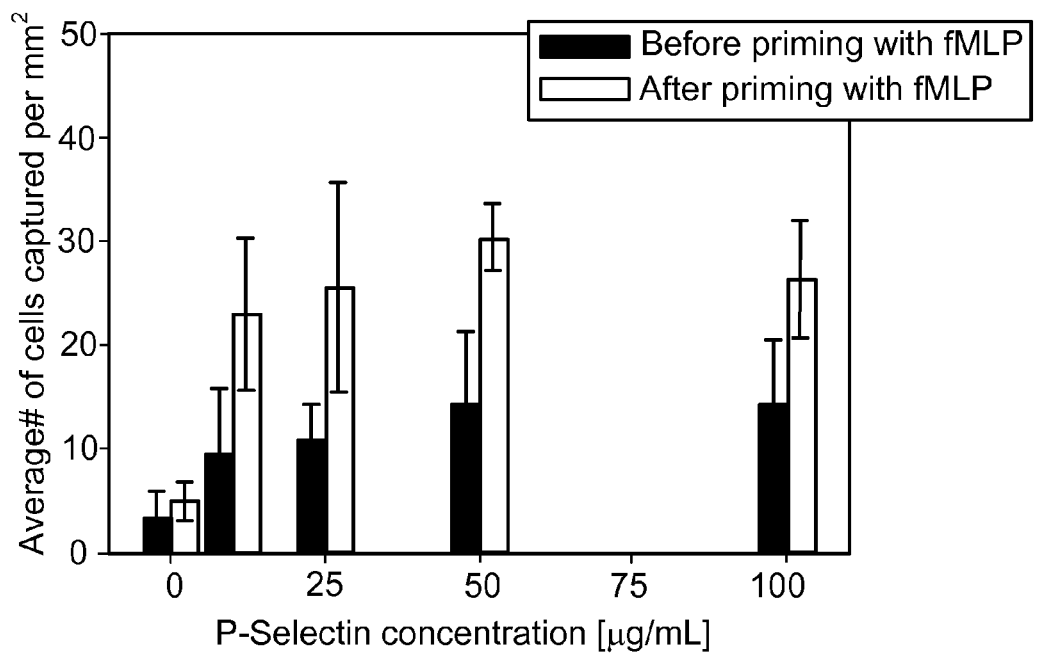
Figure 6C:
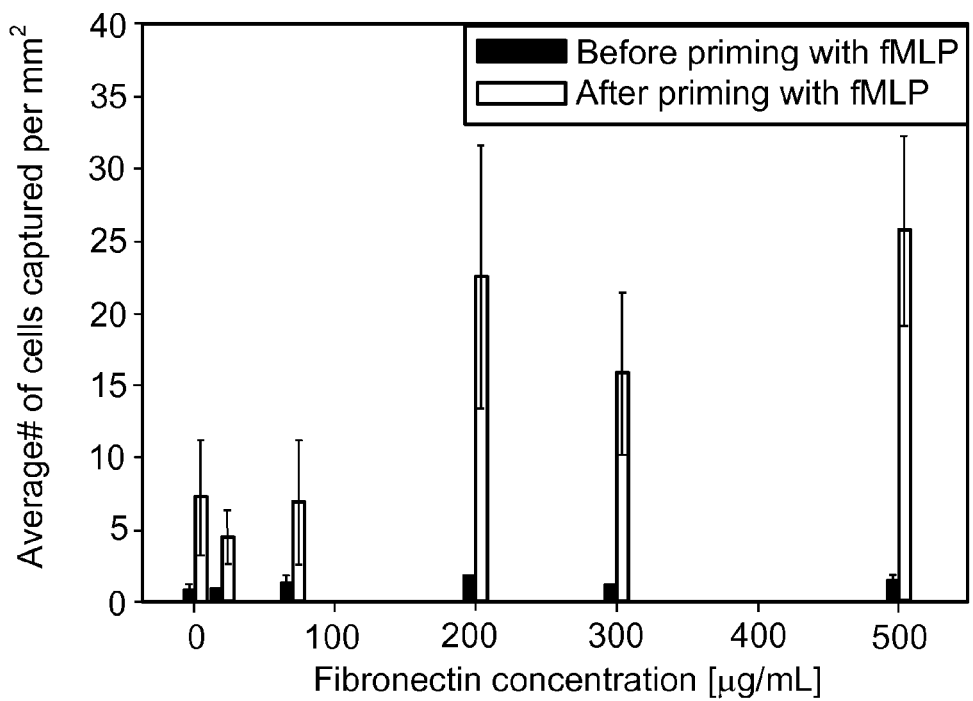

The neutrophil isolation on substrates coated with three different cell adhesion molecules (CAM) using blood samples obtained from three different individuals was characterized. The average number of cells captured per square millimeter was plotted against the concentration of CAM solution used to prepare the capture surface. The experimental data suggests that the capture efficiency for all three CAM initially increases with concentration, and then plateaus or starts descending at higher concentration value (FIGS. 6A-6C). The maximum capture efficiency for P- and E-selectins was approximately 35 and 15 cells/mm² for concentrations of 25 and 50 μg/mL, respectively. At the same time only ~3-4 cells/mm² were captured on fibronectin coated surfaces at 200 μg/mL concentration of priming solution. The statistical analysis showed that substrate concentration has significant effect ($P<<0.05$) on cell capture.

Figure 7A:
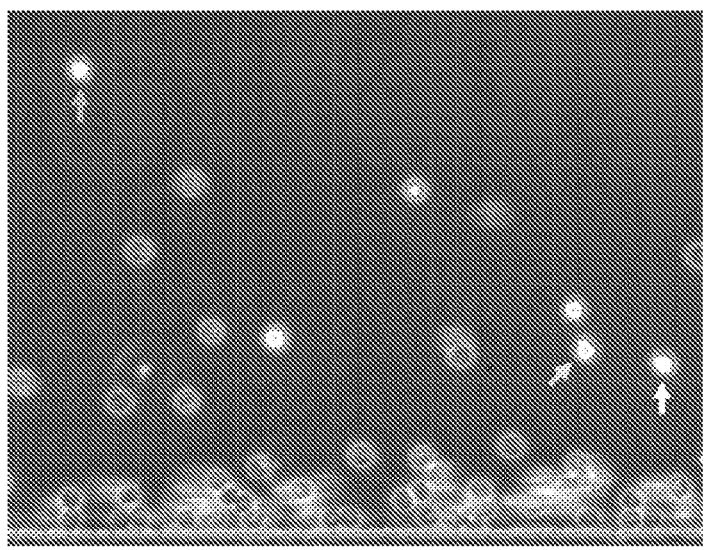
FIGS. 7A-7C are images showing morphology of neutrophils captured on a surface functionalized with P-selectin taken at 0, 1, and 5 minutes after the introduction of a chemoattractant.
Figure 7B:
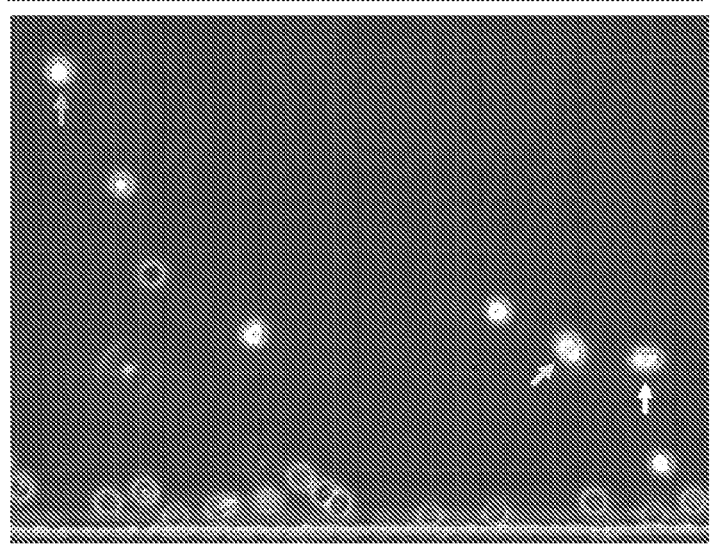
Figure 7C:
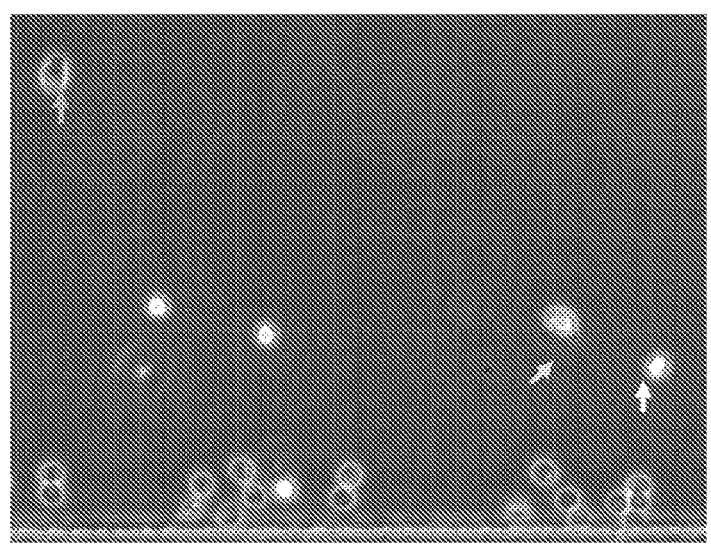

Considering an average of 5000 neutrophils/mL of blood, calculation suggests that a maximum average number of 135 neutrophils could be present in each field of view at any given time. However, an average of 20-40 cells in the field of view was captured for each experiment, and the differences may be explained by the fact that not all cells have equal chances to interact with the surface in the 5 minutes time for capture. Additionally, the interposition of red blood cells between neutrophils and the substrate could further reduce the number of neutrophils that can be captured in the microfluidic device. The morphology of the captured cells was initially spherical. As shown in FIGS. 7A-7C, cells spread on the surface only after the chemokine was introduced in the channel, suggesting that the selectin binding did not induce neutrophil activation, and the cells were captured in their quiescent state. A number of red blood cells could also be observed in the channel, which were progressively removed from the device with the fluid flow. FIGS. 7A-7C are images of neutrophils captured in a migration chamber having surfaces functionalized with P-selectin. Arrows in these figures indicate neutrophils. The position of the arrows is fixed in order to better indicate the migration of corresponding neutrophils. The observed shapes of the neutrophils were initially round (FIG. 7A), and after about one minute a change in their morphology was observed (FIG. 7B). After about 5 minutes, the cells appeared to be fully polarized, with a leading edge formed in the direction of migration (FIG. 7C).

Effect of Chemokine Exposure on Neutrophil Capture

To identify whether the chemoattractant exposure has any significant effect on neutrophil capture from whole blood, the CAM coated channel was primed with 20 nM fMLP, and the cells were captured in a similar manner as described above. The effects of chemotactic priming of channels appeared significant from the statistical analysis ($P<<0.05$). However, the comparison of capture data in primed vs. unprimed conditions, shows that approximately twice as many cells were captured over the primed E-selectin, and five times more cells on the primed fibronectin surfaces were compared to the unexposed surface. The difference was not significant in the case of P-selectin coated surfaces. Moreover, most cells were firmly adhered to the surface, and no rolling was observed for the treated channels. The statistical analysis suggests that there is no interaction between substrates, concentration and priming conditions.

Neutrophil Migration Assay

Figure 8A:
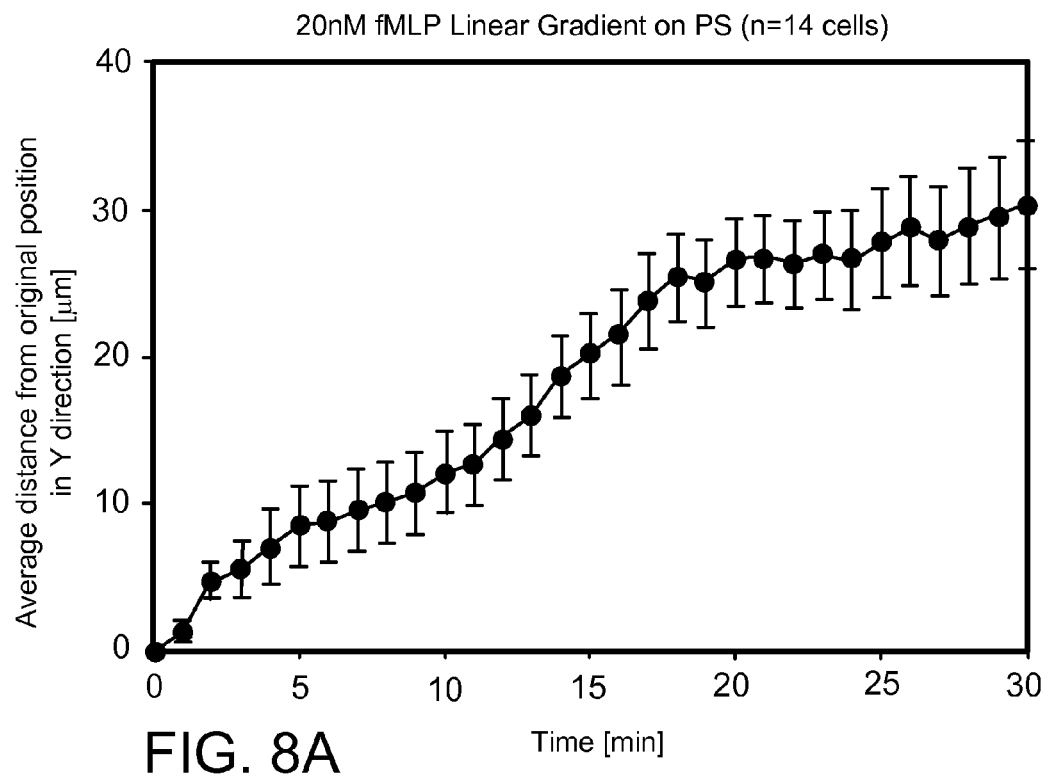
FIGS. 8A-8F show exemplary data obtained using optical techniques for neutrophil migration on surfaces functionalized with P-selectin, E-selectin, and fibronectin.
Figure 8B:
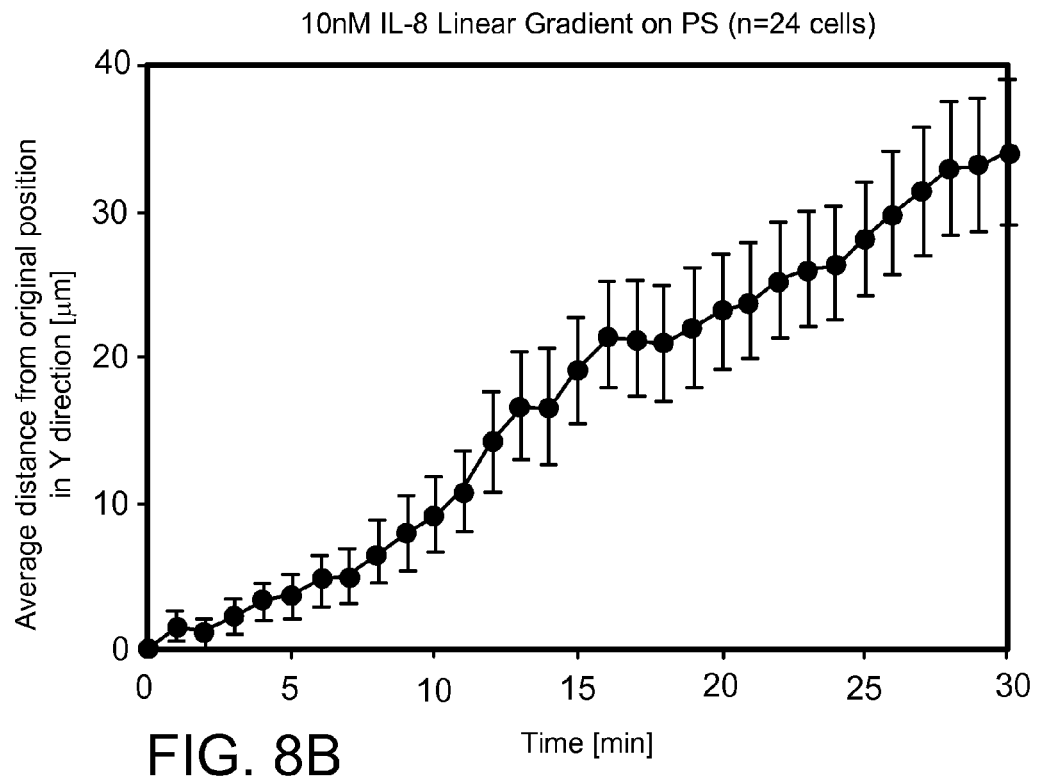
Figure 8C:
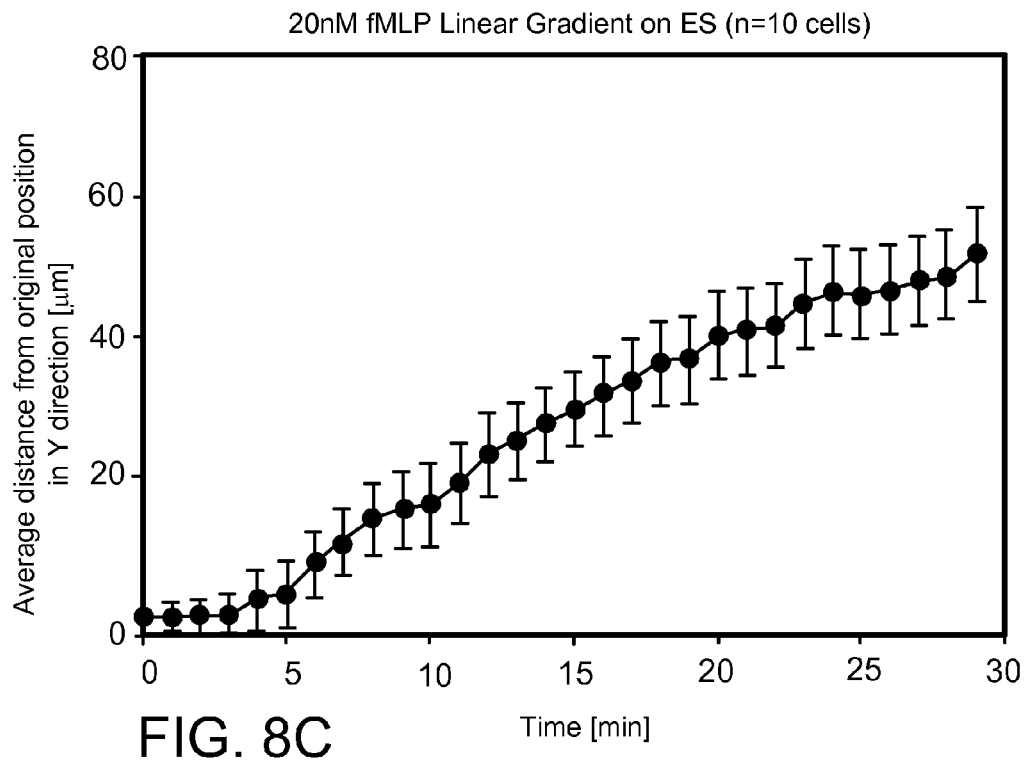
Figure 8D:
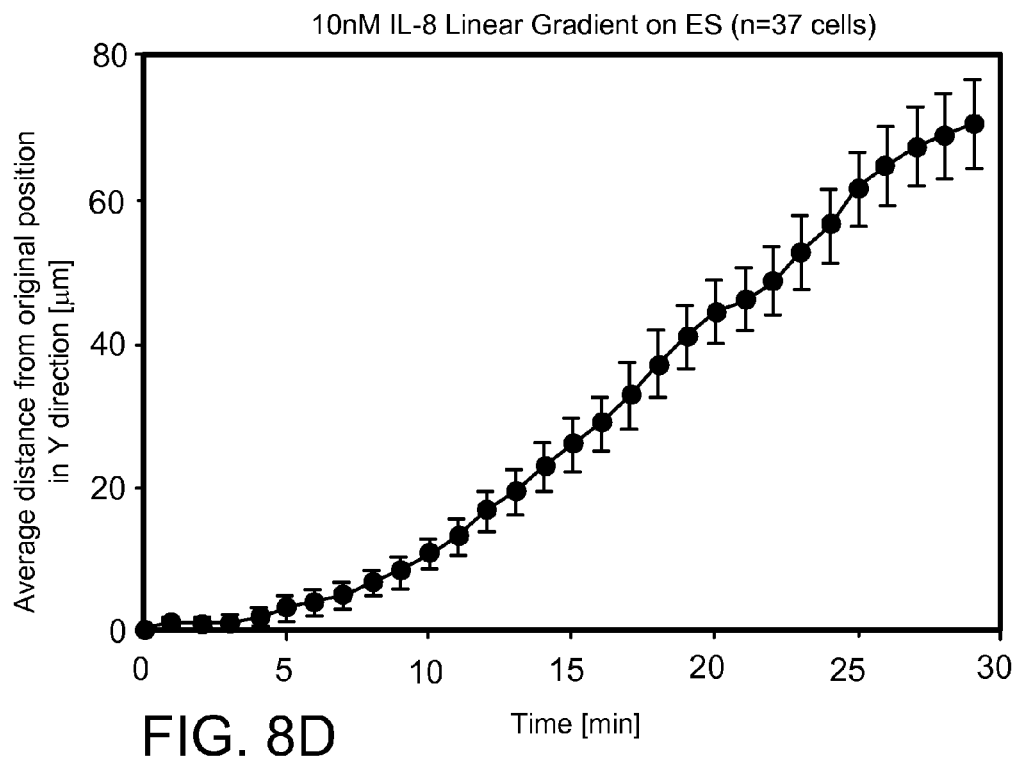
Figure 8E:
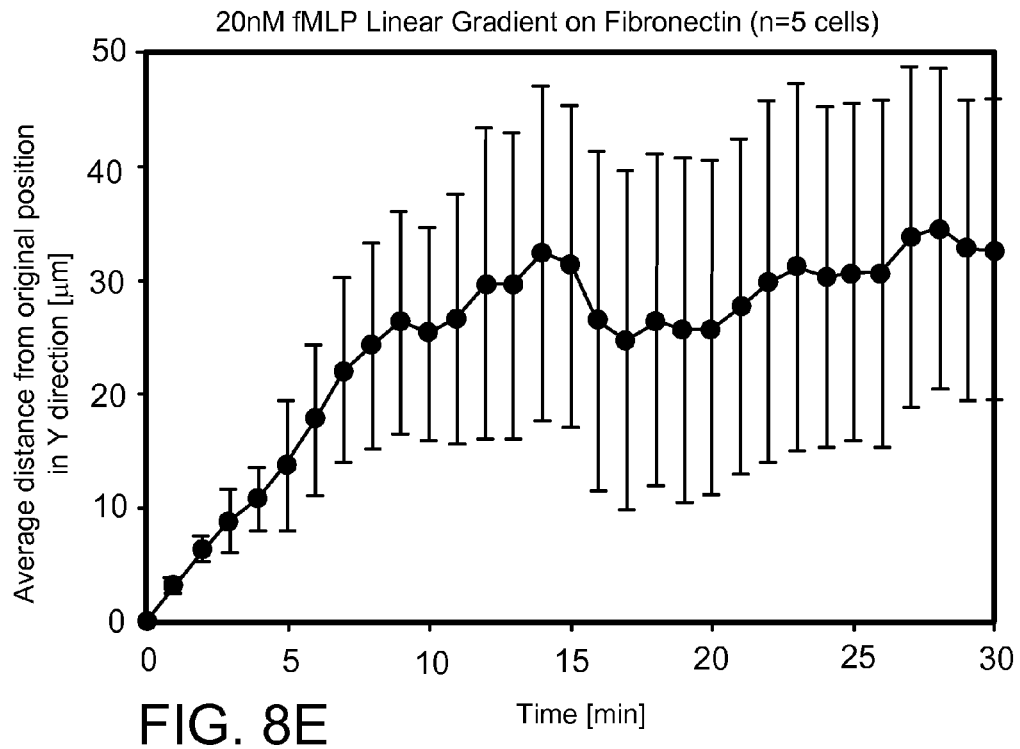
Figure 8F:
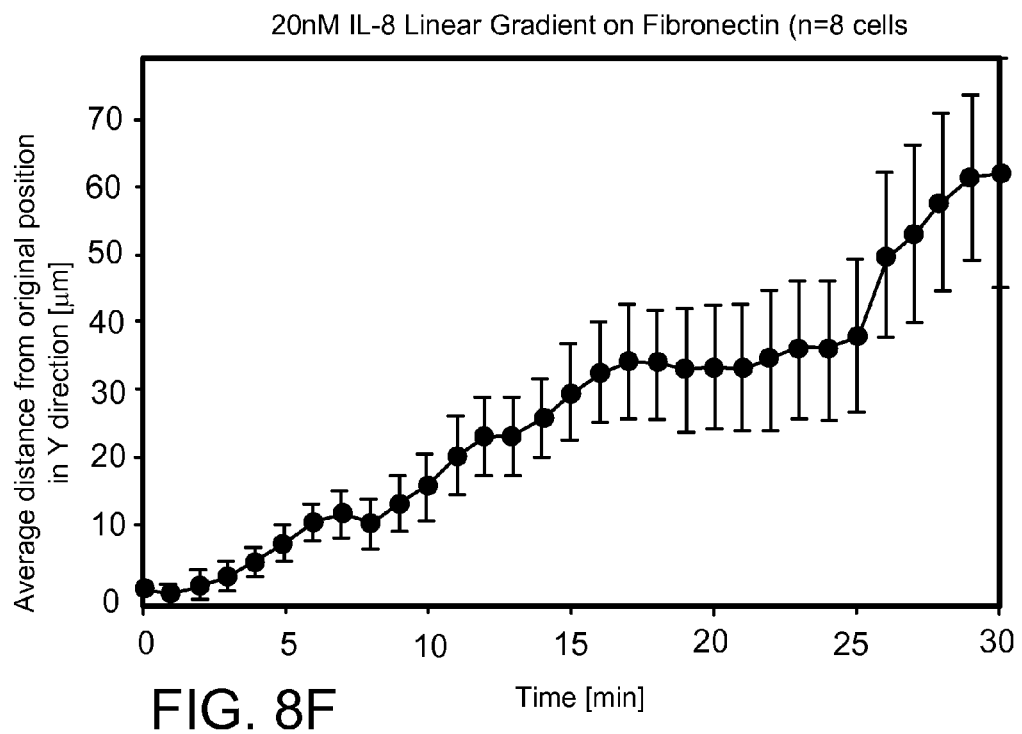

After determining the optimized conditions for maximum cell capture efficiency, the migration experiment was performed using the switching gradient device (FIGS. 2C and 2D). Two different chemoattractants were individually used to create a gradient over each binding substrate. Each experiment was repeated 2-3 times with fresh blood samples from different donors and migration data for at least 10 and up to 40 cells were averaged for each case. Average distance traveled in the direction of the gradient is plotted against time. Both IL8 and fMLP gradients yield similar velocity curves over P-selectin, and average displacements of around 30-40 μm were observed in 30 minutes, as presented in FIGS. 8A and 8B. In the presence of E-selectin and gradients of fMLP and IL8, average displacements of 50 μm and 70 μm respectively were observed, within the first 30 minutes, (FIGS. 8C and 8D). In the presence of fibronectin, the cells migrated about 65 μm in fMLP and only 35 μm in IL8 gradients in 30 minutes, as shown in FIGS. 8E and 8F.

FIGS. 8A-8F show the average neutrophil migration on P-selectin, E-selectin, and fibronectin coated substrates: (A) Neutrophil migration on 25 μg/mL P-selectin surface in the presence of 20 nM/450 μm fMLP gradient; (B) Neutrophil migration over P-selectin surface in the presence of 10 nM/450 μm IL-8 gradient; (C) Neutrophil migration over 50 μg/mL E-selectin in the presence of 20 nM/450 μm fMLP gradient; (D) Neutrophil migration over E-selectin in the presence of 10 nM/450 μm IL-8 gradient; (E) Neutrophil migration over 200 μg/mL fibronectin in the presence of 20 nM/450 μm fMLP gradient; and (F) Neutrophil migration over fibronectin in the presence of 10 nM/450 μm IL-8 gradient. Error bars in all figures represent standard error of the mean.

From the directional analysis, the random motility coefficient (μ) and the directional persistence time (P) were calculated for the initial 10 minutes of migration, and the mean values for about 15 cells for each condition (except fibronectin where capture efficiency was low and less than 10 cells were observed) are given in Table 2. Migration analysis suggests that the migration profile was more directionally biased and persistent for P-selectin, compared to the other two substrates. Also when the effects of the two chemoattractants are compared, fMLP demonstrated greater directional bias than IL8 for all three substrates.

TABLE 2

Migration analysis and motility parameters at various conditions

| Substrate CAM | Chemokine | Persistence time (P) (minutes) | Random motility coefficient (μ) (μm²/minute) |
|---|---|---|---|
| P-selectin | fMLP | 4.09 | 8.07 |
| P-selectin | IL-8 | 3.77 | 14.89 |
| E-selectin | fMLP | 2.64 | 23.64 |
| E-selectin | IL-8 | 3.79 | 33.92 |
| Fibronectin | fMLP | 3.22 | 17.7 |
| Fibronectin | IL-8 | 3.83 | 27.01 |

Discussion

Neutrophil rolling and adhesion mechanisms under varying shear stresses have been rigorously studied and well characterized. While it is widely accepted that different selectins play unique roles in neutrophil trafficking, binding and migration patterns of freshly isolated primary neutrophils on selectin substrates were observed. In vitro, the selectins not only facilitate neutrophil isolation from peripheral blood but can also allow migration on a surface in the presence of a chemotactic gradient. By comparing capturing efficiencies of substrates coated with P-selectin, E-selectin, and fibronectin at various concentrations, each substrate has a threshold concentration value for which a maximum number of cells are captured. If the priming solutions contain chemoattractants, more neutrophils can be isolated on the same CAM coated surface; however, subsequent motility may be affected.

The selective capture of leukocyte subpopulation (neutrophils) is important, and it has been previously shown that neutrophils can be preferentially captured using P- and E-selectin substrates with 90-98% purity. Among the contaminant cells are monocytes and lymphocytes. While some monocytes could to respond to the same chemotactic stimuli as neutrophils, they can be easily differentiated from neutrophils based on their larger size. An overall uniform size distribution of the captured cells suggesting that most of the captured leukocytes were neutrophils was observed. The observed average migration velocities in the direction transversal to the channel were comparable with previous findings where migration of HL60 cells over fibronectin was investigated under similar flow conditions.

Further Migration Analysis

Figures 9A, 9B:
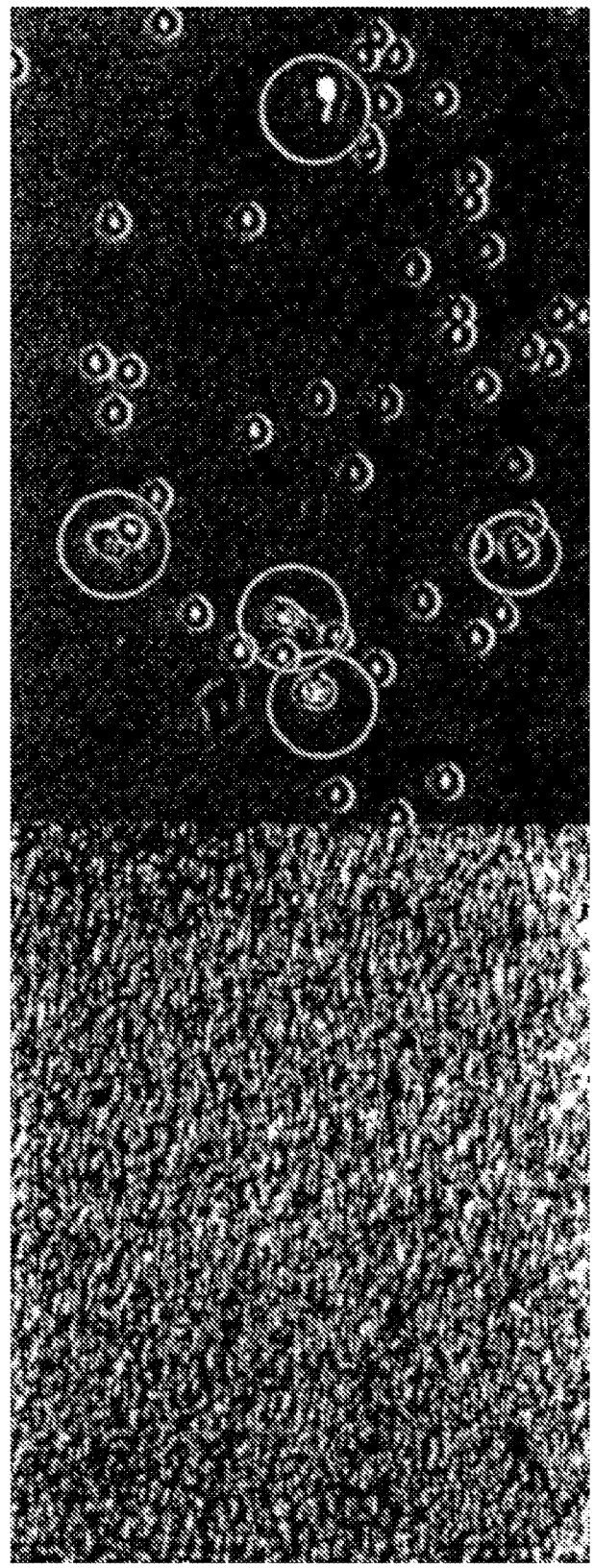
FIG. 9A is an image of a whole blood sample as it flows through a migration chamber.
FIG. 9B is an image of neutrophils captured on the surface of a migration chamber functionalized with P-selectin after red blood cells have been washed away.

The surface of the migration chamber of a device as described herein was functionalized with P-selectin by exposure to a 10 nM solution of P-selectin for 10 minutes, followed by Hanks buffer wash for 5 minutes. Capillary blood was collected from the tip of a finger using a lancet. A volume of 10 μL (equivalent of a small droplet) was collected in 10 μL heparin 2×, mixed well by repeated pipetting, and introduced into the device. After filling the main channel, a slow flow rate of the blood was established by raising the inlet tube at 4-5 cm above the level of the device. An image of the blood sample in the migration chamber is shown in FIG. 9A.

After 5 minutes, the blood inlet was clamped, and buffer was introduced from one of the gradient generators that had Hanks buffer solution at both inlets. After 1 minute of washing all the red blood cells through the device, only leukocytes were left on the P selectin coated surface of the migration chamber. Based on observed morphological characteristics, most of the remaining captured cells appeared to be neutrophils. After 5-10 minutes of washing using a buffer, a gradient of IL-8 (from 0 to 12 nM over 400 μm distance) was rapidly established using the second gradient chamber. An immediate response of the neutrophils to exposure to the IL-8 gradient was observed, including formation of protrusions that would later develop into leading edge and uropod (FIG. 9B).

Figure 10:
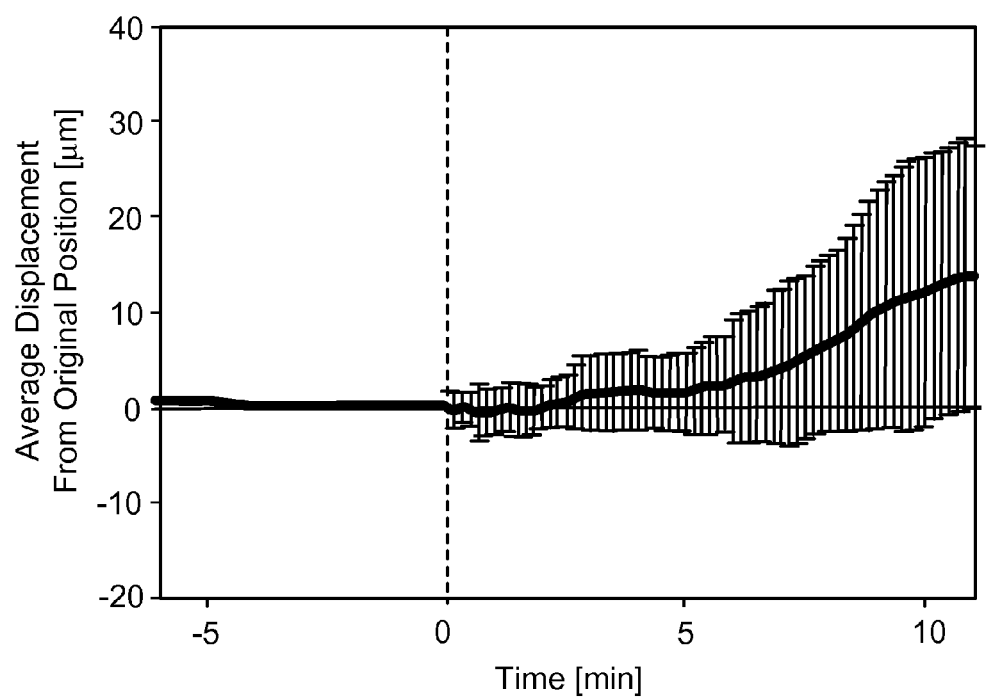
FIG. 10 is a graph showing migration of neutrophils in a gradient of IL-8 as a function of time.

The displacement of neutrophils in the direction of the gradient was also measured as a function of time. Data for 20 observed cells was collected and averaged, and is presented in FIG. 10.

No significant chemokinesis of neutrophils on a substrate functionalized with P-selectin was observed in the absence of IL-8. This observation suggests that neutrophils may not be activated by contact with the P-selectin coated surface. A few minutes after establishing a chemoattractant IL-8 gradient, neutrophils were observed to display sustained migration in the direction of the gradient.

Other Embodiments

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. In addition, all publications, patents, and patent applications referenced above are incorporated herein by reference in their entireties.

Other embodiments are in the claims.

What is claimed is:

1. A system for assessing migration of biological particles in a gradient, comprising:
   at least one migration chamber configured to contain a biological sample;
   at least one gradient arrangement configured to provide at least one predetermined gradient within the migration chamber; and
   a detection arrangement configured to determine spatial information associated with biological particles within the migration chamber, wherein the spatial information of the biological particles relates to the migration of the biological particles based on the at least one predetermined gradient, wherein the detection arrangement further comprises a plurality of channels provided within a portion of the at least one migration chamber, and wherein at least one sensor is associated with each channel.

2. The system of claim 1, wherein the detection arrangement comprises a plurality of detectors arranged at an end of the migration chamber.

3. The system of claim 1, wherein a volume of the biological sample is less than 20 μL.

4. The system of claim 1, wherein a dimension of the at least one migration chamber is less than 1 mm.

5. The system of claim 1, wherein the detection arrangement comprises at least one of an optical microscope or a digital imaging arrangement.

6. The system of claim 1, wherein the detection arrangement comprises a plurality of sensors provided proximal to a distal portion of the at least one migration chamber.

7. The system of claim 6, wherein at least one sensor comprises an optical sensor configured to detect at least one biological particle or an electrical sensor configured to detect at least one biological particle based on at least one of an impedance signal or a conductance signal.

8. The system of claim 1, wherein each sensor associated with a particular channel is configured to detect each biological particle passing through the particular channel.

9. The system of claim 1, wherein the spatial information comprises at least one of a spatial distribution, a profile, a location, and/or a coordinate associated with the plurality of the biological particles within the at least one migration chamber.

10. The system of claim 9, wherein the information is based on the spatial locations obtained at a particular time.

11. The system of claim 9, wherein the information is based on the spatial locations obtained at a plurality of times.

12. The system of claim 1, wherein the at least one predetermined gradient is at least one of a temperature gradient, light intensity gradient, an electrical field gradient, and/or a magnetic field gradient.

13. The system of claim 1, wherein the at least one predetermined gradient comprises at least one gradient in concentration of at least one substance across at least a portion of the at least one migration chamber.

14. The system of claim 13, wherein the at least one gradient is provided across a lateral width of the at least one migration chamber.

15. The system of claim 13, wherein the at least one gradient arrangement comprises a first gradient chamber configured to contain a particular solution comprising the at least one substance and a second gradient chamber configured to contain a further solution with an average concentration of the at least one substance that is different than the average concentration of the at least one substance in the particular solution.

16. The system of claim 15, comprising valves controlling fluid flow from the first and second gradient chambers to the at least one migration chamber, wherein the valves operate to change the gradient within at least a portion of the at least one migration chamber at a particular time.

17. The system of claim 1, wherein a surface of the at least one migration chamber is configured to bind to or isolate the biological particles from the biological sample or to bind to and isolate the biological particles from the biological sample.

18. The system of claim 17, wherein the surface comprises at least one binding moiety capable of binding to the biological particles.

19. The system of claim 18, wherein the biological particles are neutrophils, and the at least one binding substance comprises at least one of an antibody, a selectin, P-selectin, E-selectin, V-CAM, and fibronectin.

20. The system of claim 18, wherein the at least one binding substance comprises a carbohydrate-binding protein capable of binding to at least one of a glycoprotein or a glycolipid present on a surface of the biological particles.

21. A method for assessing migration of biological particles in a gradient, comprising:
providing a biological sample in a system comprising at least one migration chamber configured to contain the biological sample, wherein the biological sample comprises a plurality of the biological particles; at least one gradient arrangement configured to provide at least one predetermined gradient within the migration chamber; and a detection arrangement configured to determine spatial information associated with the biological particles within the migration chamber;
providing at least one predetermined gradient within the migration chamber; and
determining spatial information associated with the biological particles within the migration chamber, wherein the spatial information of the biological particles relates to the migration of the biological particles based on the at least one predetermined gradient, and wherein a surface of the migration chamber comprises a binding moiety for the biological particles.

22. The method of claim 21, wherein the detection arrangement comprises a plurality of detectors arranged at an end of the migration chamber.

23. The method of claim 21, wherein the size of the biological sample is less than about 20 µL.

24. The method of claim 21, wherein the biological sample comprises whole blood, biological particles are neutrophils, and the binding moiety comprises at least one of an antibody, selectin, P-selectin, E-selectin, V-CAM, and/or fibronectin.

25. The method of claim 21, wherein the at least one gradient is provided across a lateral width of the at least one migration chamber.

26. The method of claim 21, further comprising at least two gradients across a lateral width of the at least one migration chamber.

27. The method of claim 26, wherein each of the at least two gradients is provided at a different time.

28. The method of claim 21, wherein the gradient comprises a concentration gradient of at least one substance.

29. The method of claim 28, wherein the at least one substance comprises at least one of a chemokine, a chemoattractant, or both.

30. The method of claim 28, wherein the at least one substance comprises at least one of a CC chemokine, CXC chemokine, C chemokine, CX3C chemokine, ELR-positive CXC chemokine, interleukin-8, leukotriene B4, zymosan-activated serum, an N-formylated peptide, MCP-I, CCL28, CCL5, CXCL13, XCL1, XCL2, fractalkine C5a, SDF 1, and N-formyl-methionyl-leucyl-phenylalanine.

31. The method of claim 21, wherein the at least one gradient comprises a concentration gradient of a chemical species capable of inhibiting migration of the biological particles.

32. The method of claim 21, wherein said at least one gradient comprises a candidate therapeutic agent, and the spatial information is indicative of the effect of the candidate therapeutic agent on the migration of the biological particles.

* * * * *

UNITED STATES PATENT AND TRADEMARK OFFICE
CERTIFICATE OF CORRECTION

PATENT NO. : 8,921,122 B2  
APPLICATION NO. : 12/867160  
DATED : December 30, 2014  
INVENTOR(S) : Daniel Irimia Page 1 of 1

It is certified that error appears in the above-identified patent and that said Letters Patent is hereby corrected as shown below:

Title Page 2, Column 2, Line 13:

(56) Other Publications

Delete "Anal" and Insert -- Anat --

In the Claims

Column 26, Claim 23, Line 28:

After "than" Delete "about"

Signed and Sealed this
Fifth Day of May, 2015

Michelle K. Lee
*Director of the United States Patent and Trademark Office*